United States Patent
D'Amico et al.

(10) Patent No.: US 10,267,027 B2
(45) Date of Patent: Apr. 23, 2019

(54) URINAL SCREENS

(71) Applicant: GPCP IP Holdings LLC, Atlanta, GA (US)

(72) Inventors: Daniel D'Amico, South Salem, NY (US); Eric Peterson, Mount Horeb, WI (US); Todd Lappi, Atlanta, GA (US); Jacob Edward Malesky, Menasha, WI (US)

(73) Assignee: GPCP IP HOLDINGS LLC, Atlanta, GA (US)

( * ) Notice: Subject to any disclaimer, the term of this patent is extended or adjusted under 35 U.S.C. 154(b) by 0 days.

(21) Appl. No.: 15/285,951

(22) Filed: Oct. 5, 2016

(65) Prior Publication Data
US 2017/0096808 A1 Apr. 6, 2017

Related U.S. Application Data

(60) Provisional application No. 62/237,276, filed on Oct. 5, 2015.

(51) Int. Cl.
| | |
|---|---|
| *E03D 1/26* | (2006.01) |
| *E03D 13/00* | (2006.01) |
| *A61L 9/01* | (2006.01) |
| *A61L 9/05* | (2006.01) |

(52) U.S. Cl.
CPC .............. *E03D 13/005* (2013.01); *A61L 9/01* (2013.01); *A61L 9/05* (2013.01)

(58) Field of Classification Search
CPC .......... E03D 13/005; E03D 9/005; A61L 9/12
See application file for complete search history.

(56) References Cited

U.S. PATENT DOCUMENTS

| | | | |
|---|---|---|---|
| 571,275 A | 11/1896 | Maxwell et al. | |
| 647,895 A | 4/1900 | Burson | |
| 675,947 A | 6/1901 | Hach | |
| 683,419 A | 9/1901 | Burson | |
| 927,026 A * | 7/1909 | Clayton .................. | E03D 13/00 210/499 |
| 1,186,345 A | 6/1916 | Sleight | |
| 1,430,598 A | 10/1922 | Sleight | |
| 2,046,214 A | 6/1936 | Selig | |

(Continued)

FOREIGN PATENT DOCUMENTS

| | | |
|---|---|---|
| AU | 636863 B | 6/1991 |
| AU | 2015100064 A4 | 2/2015 |

(Continued)

OTHER PUBLICATIONS

U.S. Appl. No. 29/541,529, Georgia-Pacific Consumer Products.

(Continued)

*Primary Examiner* — Huyen Le
(74) *Attorney, Agent, or Firm* — Eversheds Sutherland (US) LLP

(57) ABSTRACT

Embodiments of the present invention provide urinal screens for reduced splashing. The urinal screen includes an outer ring and a web portion. The web portion includes a plurality of web strings disposed in a mesh pattern such that a plurality of open areas are defined between the web strings. Portions of the web strings forming a first face of the web portion configured to receive urine in use are substantially rounded in profile.

24 Claims, 26 Drawing Sheets

(56) References Cited

U.S. PATENT DOCUMENTS

| | | |
|---|---|---|
| 2,211,970 A | 8/1940 | Fischer |
| 2,718,013 A | 9/1955 | Rajnicek |
| 2,813,631 A | 11/1957 | Odman |
| 2,974,324 A | 3/1961 | Lundelius |
| D194,776 S | 3/1963 | Clark |
| D194,777 S * | 3/1963 | Clark ................ D23/261 |
| 3,170,169 A | 2/1965 | Clark |
| 3,248,740 A | 5/1966 | Wisnom |
| 3,597,772 A | 8/1971 | Leavitt |
| 3,760,429 A | 9/1973 | Brownstein |
| 3,994,439 A | 11/1976 | Van Breen et al. |
| 4,044,405 A | 8/1977 | Kreiss |
| 4,095,031 A | 6/1978 | Engle |
| 4,103,367 A | 8/1978 | Kaufer |
| 4,135,261 A | 1/1979 | Uhrman |
| D253,145 S | 10/1979 | Adam |
| D253,146 S | 10/1979 | Adam |
| D255,744 S | 7/1980 | Dekko |
| 4,215,443 A | 8/1980 | Babik |
| D258,181 S | 2/1981 | Adam |
| D258,472 S | 3/1981 | Adam |
| D259,225 S | 5/1981 | Scheer |
| 4,492,644 A | 1/1985 | Matsumoto et al. |
| 4,552,692 A | 11/1985 | Gillespie |
| 4,574,400 A | 3/1986 | Annowksy |
| 4,574,403 A | 3/1986 | Dintemann et al. |
| 4,671,976 A * | 6/1987 | Vidal ................ A47K 1/14 4/286 |
| 4,761,437 A | 8/1988 | Christie |
| 5,019,346 A | 5/1991 | Richter et al. |
| D329,893 S | 9/1992 | Luedtke et al. |
| 5,165,119 A | 11/1992 | Yamato |
| D332,302 S | 1/1993 | Brown |
| D336,948 S | 6/1993 | Frankel |
| 5,312,624 A | 5/1994 | Richter et al. |
| 5,313,672 A | 5/1994 | Luedtke et al. |
| 5,336,424 A | 8/1994 | Van Vlahakis et al. |
| 5,365,616 A | 11/1994 | Morad |
| D353,445 S | 12/1994 | Morad |
| 5,379,917 A | 1/1995 | Brown et al. |
| D355,807 S | 2/1995 | O'Rourke |
| 5,398,347 A | 3/1995 | Luedtke et al. |
| 5,489,415 A | 2/1996 | Van Vlahakis et al. |
| D370,938 S | 6/1996 | Roach |
| 5,567,389 A | 10/1996 | Birbara et al. |
| 5,595,324 A | 1/1997 | Brown et al. |
| 5,604,937 A | 2/1997 | Davenport |
| D393,896 S | 4/1998 | Wagner et al. |
| 5,774,905 A | 7/1998 | Wagner et al. |
| 5,799,826 A | 9/1998 | Brown et al. |
| 5,809,590 A | 9/1998 | Williams et al. |
| 5,813,058 A | 9/1998 | Quigley et al. |
| D410,281 S | 5/1999 | Walker |
| 6,055,681 A | 5/2000 | Lyons |
| 6,062,425 A | 5/2000 | Brown et al. |
| D427,295 S | 6/2000 | Wagner |
| D428,120 S | 7/2000 | Zaldivar |
| 6,081,937 A | 7/2000 | Whitacre |
| 6,197,321 B1 | 3/2001 | Richter et al. |
| 6,269,490 B1 | 8/2001 | Suski et al. |
| D456,492 S | 4/2002 | Lourens |
| D464,122 S | 10/2002 | Mangan |
| D479,313 S | 9/2003 | Navarra |
| 6,631,852 B1 | 10/2003 | O'Leary |
| 6,640,350 B1 | 11/2003 | Deutsch |
| D486,341 S | 2/2004 | Ruhl |
| 6,698,035 B1 | 3/2004 | Grueser |
| 6,729,506 B2 | 5/2004 | Brown et al. |
| 6,769,631 B2 | 8/2004 | Brown |
| 6,823,533 B2 | 11/2004 | Casari |
| 6,920,648 B1 | 7/2005 | Suski et al. |
| D520,610 S | 5/2006 | Wrate |
| 7,100,801 B2 | 9/2006 | Brown et al. |
| D530,215 S | 10/2006 | Brown et al. |
| 7,202,201 B1 | 4/2007 | Williams |
| D550,819 S | 9/2007 | Seehoff |
| D552,308 S | 10/2007 | Farr |
| 7,325,694 B2 | 2/2008 | Bushey |
| D564,550 S | 3/2008 | Pinchot |
| D564,551 S | 3/2008 | Pinchot |
| D565,067 S | 3/2008 | Pinchot |
| D565,610 S | 4/2008 | Pinchot |
| D565,611 S | 4/2008 | Pinchot |
| D565,612 S | 4/2008 | Pinchot |
| D565,613 S | 4/2008 | Pinchot |
| D565,614 S | 4/2008 | Pinchot |
| D565,615 S | 4/2008 | Pinchot |
| D566,145 S | 4/2008 | Pinchot |
| D568,349 S | 5/2008 | Pinchot |
| D571,898 S | 6/2008 | Gilligan |
| 7,398,565 B1 | 7/2008 | Chou |
| 7,410,513 B2 | 8/2008 | Requejo et al. |
| D577,416 S | 9/2008 | Buttgen |
| 7,461,413 B2 | 12/2008 | Lewis et al. |
| D584,863 S | 1/2009 | Garry |
| 7,484,675 B2 | 2/2009 | Brown |
| 7,597,949 B2 | 10/2009 | Wright |
| 7,618,532 B2 | 11/2009 | Worth |
| D612,914 S | 3/2010 | Morad |
| 7,735,694 B2 | 6/2010 | Brown et al. |
| D625,540 S | 10/2010 | Dukes |
| D629,636 S | 12/2010 | Wright |
| D629,875 S | 12/2010 | Sears |
| D630,306 S | 1/2011 | Seehoff et al. |
| D630,714 S | 1/2011 | Dukes |
| D631,531 S | 1/2011 | Morad |
| 7,887,697 B2 | 2/2011 | Worth |
| D639,410 S | 6/2011 | Ramirez |
| D642,003 S | 7/2011 | Wright |
| 8,007,707 B1 | 8/2011 | Brown et al. |
| 8,043,606 B2 | 10/2011 | MacBeth et al. |
| D655,793 S | 3/2012 | Emr |
| 8,127,969 B2 | 3/2012 | Brown et al. |
| D662,573 S | 6/2012 | Rogalski |
| D664,571 S | 7/2012 | Beyer |
| D678,482 S | 3/2013 | Williams |
| D678,483 S | 3/2013 | Barker |
| D686,255 S | 7/2013 | Fu |
| D687,471 S | 8/2013 | Fu |
| D699,819 S | 2/2014 | Tung |
| 8,856,977 B2 | 10/2014 | Ramirez |
| D718,844 S | 12/2014 | Johansen |
| D718,845 S | 12/2014 | Johansen |
| 8,916,140 B2 | 12/2014 | MacBeath et al. |
| D724,702 S | 3/2015 | D'Amico |
| 8,974,736 B2 | 3/2015 | Brown et al. |
| D726,886 S | 4/2015 | Sutherland |
| D730,493 S | 5/2015 | Sehl |
| 9,027,172 B2 | 5/2015 | Fima |
| D743,509 S | 11/2015 | Traub et al. |
| D746,955 S | 1/2016 | Corder |
| 9,243,394 B2 | 1/2016 | Brown et al. |
| D754,829 S | 4/2016 | Krombein |
| 9,303,396 B1 | 4/2016 | Pernici et al. |
| 9,309,658 B1 | 4/2016 | Pernici et al. |
| 9,334,641 B2 | 5/2016 | Kobal |
| D759,791 S | 6/2016 | Hull |
| D759,792 S | 6/2016 | Flury |
| D778,411 S | 2/2017 | Brown et al. |
| D778,412 S | 2/2017 | Brown et al. |
| D790,042 S | 6/2017 | Ramirez |
| D805,613 S | 12/2017 | D'Amico |
| D824,495 S | 7/2018 | D'Amico et al. |
| D824,496 S | 7/2018 | D'Amico et al. |
| 10,066,382 B2 | 9/2018 | Muderlak et al. |
| 2004/0034909 A1 | 2/2004 | Grueser |
| 2004/0194198 A1 | 10/2004 | Casari |
| 2006/0037128 A1 | 2/2006 | Lewis et al. |
| 2006/0260032 A1 | 11/2006 | Smartt |
| 2007/0023539 A1 | 2/2007 | Brown et al. |
| 2007/0044221 A1 | 3/2007 | Wise, Sr. |
| 2007/0186337 A1 | 8/2007 | Emr |
| 2007/0262006 A1 | 11/2007 | Worth |
| 2007/0266486 A1 | 11/2007 | Ramirez |

(56) References Cited

U.S. PATENT DOCUMENTS

| | | | |
|---|---|---|---|
| 2008/0098505 A1 | 5/2008 | Casari | |
| 2008/0280095 A1 | 11/2008 | Wright | |
| 2008/0292855 A1 | 11/2008 | Manderfield et al. | |
| 2009/0026285 A1 | 1/2009 | Worth | |
| 2010/0183694 A1 | 7/2010 | Burke et al. | |
| 2010/0199412 A1 | 8/2010 | McAlpine | |
| 2010/0257664 A1 | 10/2010 | Kener | |
| 2011/0123761 A1 | 5/2011 | Wright | |
| 2011/0289665 A1 | 12/2011 | Lees | |
| 2011/0296597 A1 | 12/2011 | Brown et al. | |
| 2012/0137419 A1 | 6/2012 | Hofeling et al. | |
| 2013/0031708 A1 | 2/2013 | Sensel | |
| 2013/0067651 A1 | 3/2013 | Brown et al. | |
| 2013/0298840 A1 | 11/2013 | Mishan | |
| 2014/0007336 A1 | 1/2014 | Mills et al. | |
| 2014/0068848 A1 | 3/2014 | Neo | |
| 2014/0075663 A1 | 3/2014 | Irwin et al. | |
| 2014/0076358 A1 | 3/2014 | Irwin et al. | |
| 2014/0076983 A1 | 3/2014 | Irwin et al. | |
| 2014/0076984 A1 | 3/2014 | Irwin et al. | |
| 2014/0076991 A1 | 3/2014 | Irwin et al. | |
| 2014/0157501 A1 | 6/2014 | D'Amico | |
| 2014/0165277 A1 | 6/2014 | Schmed et al. | |
| 2014/0250577 A1 | 9/2014 | Nakamura et al. | |
| 2014/0259344 A1 | 9/2014 | Muderlak et al. | |
| 2015/0013780 A1 | 1/2015 | Watkins | |
| 2015/0047114 A1 | 2/2015 | Ramirez | |
| 2015/0225937 A1 | 8/2015 | Brown et al. | |
| 2016/0102451 A1 | 4/2016 | Brown et al. | |
| 2016/0122992 A1 | 5/2016 | Brown et al. | |
| 2016/0215490 A1 | 7/2016 | Keune | |
| 2016/0222642 A1 | 8/2016 | Delaney | |
| 2016/0305107 A1 | 10/2016 | Muderlak et al. | |
| 2017/0067243 A1 | 3/2017 | Valencia et al. | |
| 2017/0096808 A1 | 4/2017 | D'Amico et al. | |
| 2018/0119403 A1 | 5/2018 | Crevier | |
| 2018/0305916 A1 | 10/2018 | Crevier | |

FOREIGN PATENT DOCUMENTS

| | | |
|---|---|---|
| CA | 1193199 A1 | 9/1985 |
| CN | 206346295 | 7/2017 |
| DE | 19832716 A1 | 1/2000 |
| DE | 102013108149 A1 | 2/2015 |
| GB | 2473055 A | 3/2011 |
| WO | 1994/020407 A1 | 9/1994 |
| WO | 1997/011234 A1 | 3/1997 |
| WO | 02/020172 A1 | 3/2002 |
| WO | 2004/055768 A1 | 7/2004 |
| WO | 2008/006234 A1 | 1/2008 |
| WO | 2008/089497 A1 | 7/2008 |
| WO | 2010/091862 A1 | 8/2010 |
| WO | 2014/043425 A3 | 3/2014 |
| WO | 2014/043725 A1 | 3/2014 |
| WO | 2014/093593 A1 | 6/2014 |
| WO | 2014/200400 A1 | 12/2014 |
| WO | 2015/088303 A1 | 6/2015 |
| WO | 2015/123223 A1 | 8/2015 |
| WO | 2016/060998 A1 | 4/2016 |
| WO | 2016/144153 A1 | 9/2016 |
| ZA | 200105073 A | 1/2002 |

OTHER PUBLICATIONS

U.S. Appl. No. 29/578,140, Georgia-Pacific Consumer Products.
U.S. Appl. No. 29/578,135, Georgia-Pacific Consumer Products.
U.S. Appl. No. 29/553,957, Georgia-Pacific Consumer Products.
Office Action for U.S. Appl. No. 29/578,135 dated Jul. 3, 2017, 28 pages.
HYSO HYScent Cyclone Urinal Screen—Ocean, retrieved from <https://cleaningsupply.com/catalog/p/523687EACH/HYSO-HYScent-Cyclone-Urinal-Screen-Ocean/>, on Jan. 17, 2017, 1 page.
Fresh Products, "Wave Deodorant Screen," Aug. 29, 2014 to May 26, 2015, Internet Archive <http://web.archive.org/web/*/http://freshproducts.com/wave-deodrant-screen.html>, 4 pages.
Fresh Products, "Wave 2.0", Apr. 6, 2014 to Jan. 3, 2016, Internet Archive <http://web.archive.org/web/*/http://freshproducts.com/wave-2-0.html>, 4 pages.
Impact, "Z-Screen™ Deodorizing Urinal Screens", May 2, 2014 to May 4, 2015, Internet Archive <http://web.archive.org/web/*/http://catalog.impact-products.com/viewitems/urinal-screens/z-screen%E2%84%A2-deodorizing-urinal-screens>, 2 pages.
Fresh Products, 2016 Catalog, retrieved from <http://freshproducts.com/media/wysiwyg/Literature/Fresh_Products_2016_Catalog_102915.pdf> on Jan. 26, 2016.
Hospeco, "Airworks Urinal Screens", 2 pages, retrieved from <https://www.hospeco.com/Products/AirWorks® %20Urinal%20Screens>, on Jan. 26, 2016.
Fresh Products, "Dome Urinal Screen (formerly known as RemindAir)", 2 pages, retrieved from <http://freshproducts,.com/dome-urinal-screen.html>, on Jan. 26, 2016.
Fresh Products, "Eco Bowl Clip 2.0", Mar. 27, 2014 to Jan. 16, 2016, Internet Archive <http://web.archive.org/web.archive.org/web/20160116002414/http://freshproducts.com/eco-bowl-clip.html>, 2 pages.
Hospeco, "Health Gards® Urinal Screen With Non-Para Block", 6 pages, retrieved from <https://www.hospeco.com/product/019>, on Jan. 26, 2016.
Ekcos, "ëkcoscreen", Nov. 16, 2010 to Jan. 11, 2016, Internet Archive <http://web.archive.org/web/20101116091823/http://www.wkcos.com/>, 1 page.
Rochester Midland Corporation, "Sanor Breeze Screen", Oct. 19, 2014 to Oct. 19, 2014, Internet Archive <http://web.archive.org/web/20141019152331/http://www.rochestermidland.com/products/personal_care/get_specs.cfm?PRODUCT_CODE=25190487>, 1 page.
Big D Industries, Inc., "The Pearl 3D (brochure)", 1 page, retrieved from <http://bigdind.com/product.aspx?id=BigD118>, on Jan. 26, 2016.
Fresh Products, "Toilet and Urinal—Fresh Products, Keeping Your World Smelling Fresh", retrieved from <http:/freshproducts.com/our-products/toilet-urinal, on Oct. 6, 2015, 2 pages.
Fresh Products, "Wave 3D", May 1, 2015 to Jan. 16, 2016, Internet Archive <http://web.archive.org/web/20160116045345/http://freshproducts.com/wave-3d_html>, 3 pages.
Vectair Systems, Inc., "Vectair V-Screen (brochure)", 2015, 2 pages, retrieved from <http://www.vectairsystems.com/products/washroom/v-screen-urinal-screens/>, on Jan. 26, 2016.
Ekcos, "Ekcos 30-Day Anti-Splash Protection", Copyright 2015, retrieved from <http://ekcos.com/restrooms_antisplash.html> on Mar. 3, 2016, 11 pages.
Dustbane Catalogue, "3-D Shield", Copyright 2016, retrieved from <http://www.dustbane.ca/product_sheet/en/3D_Shield_en_sm.pdf>, on Oct. 3, 2016, 1 page.

\* cited by examiner

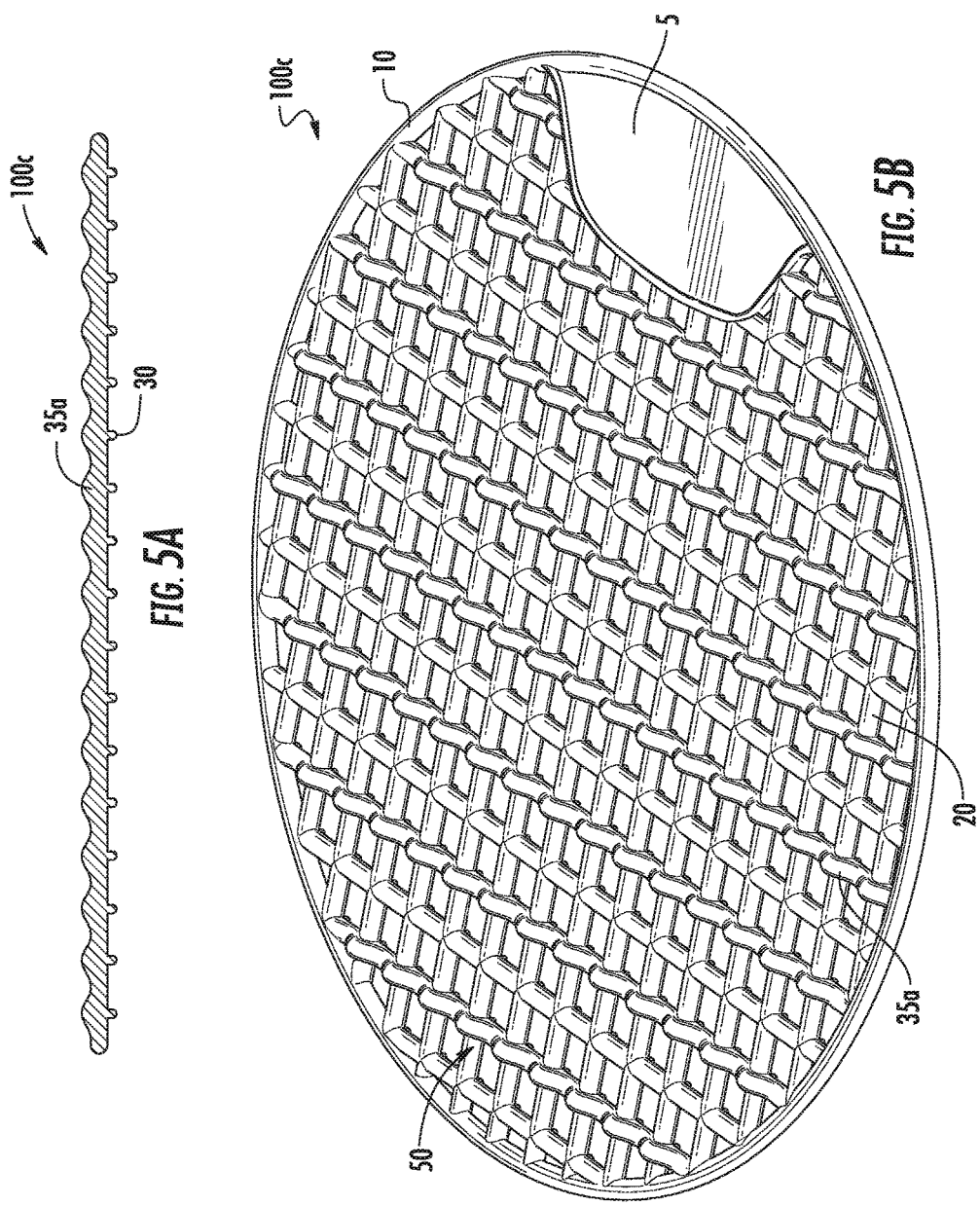

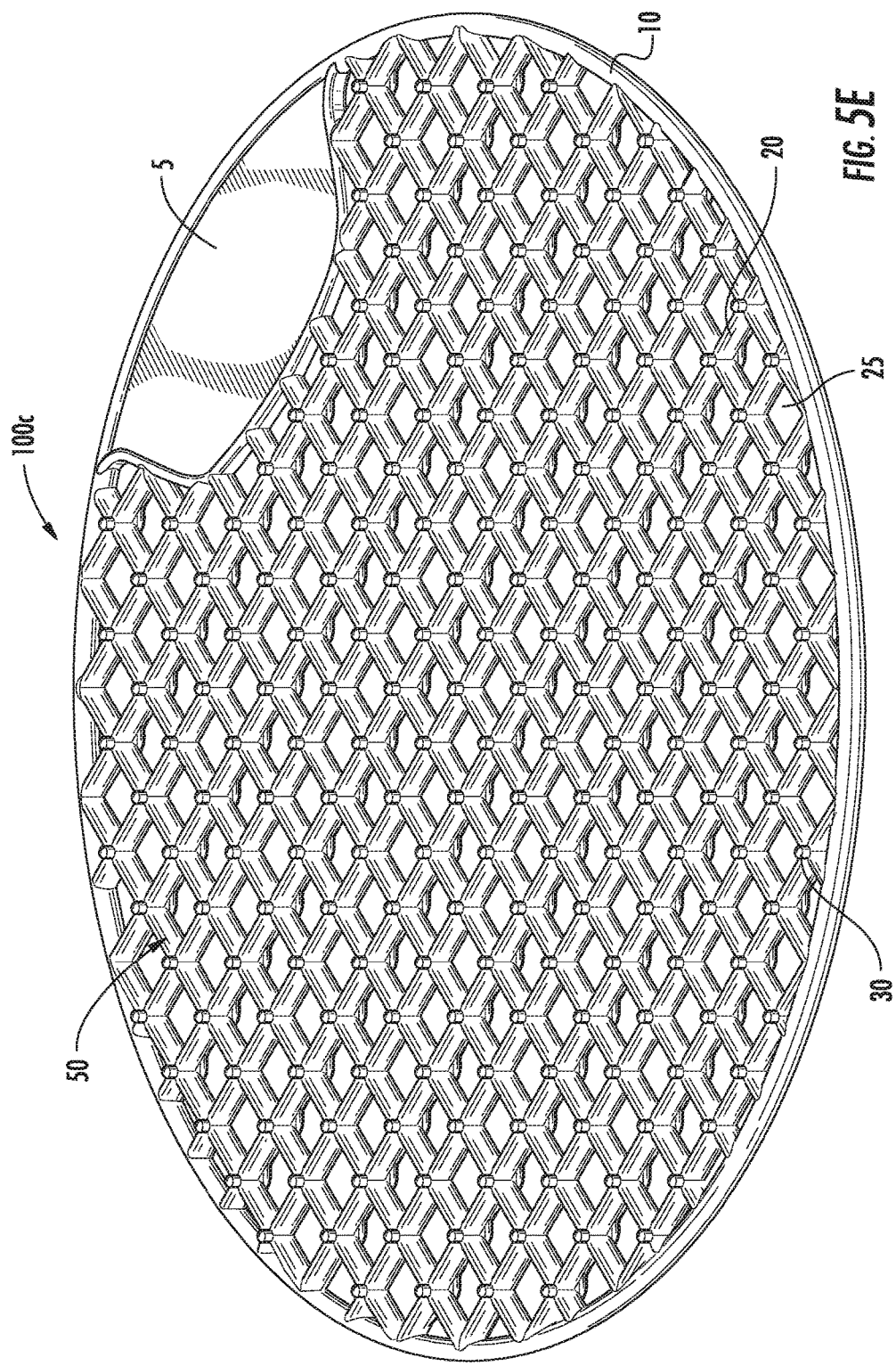

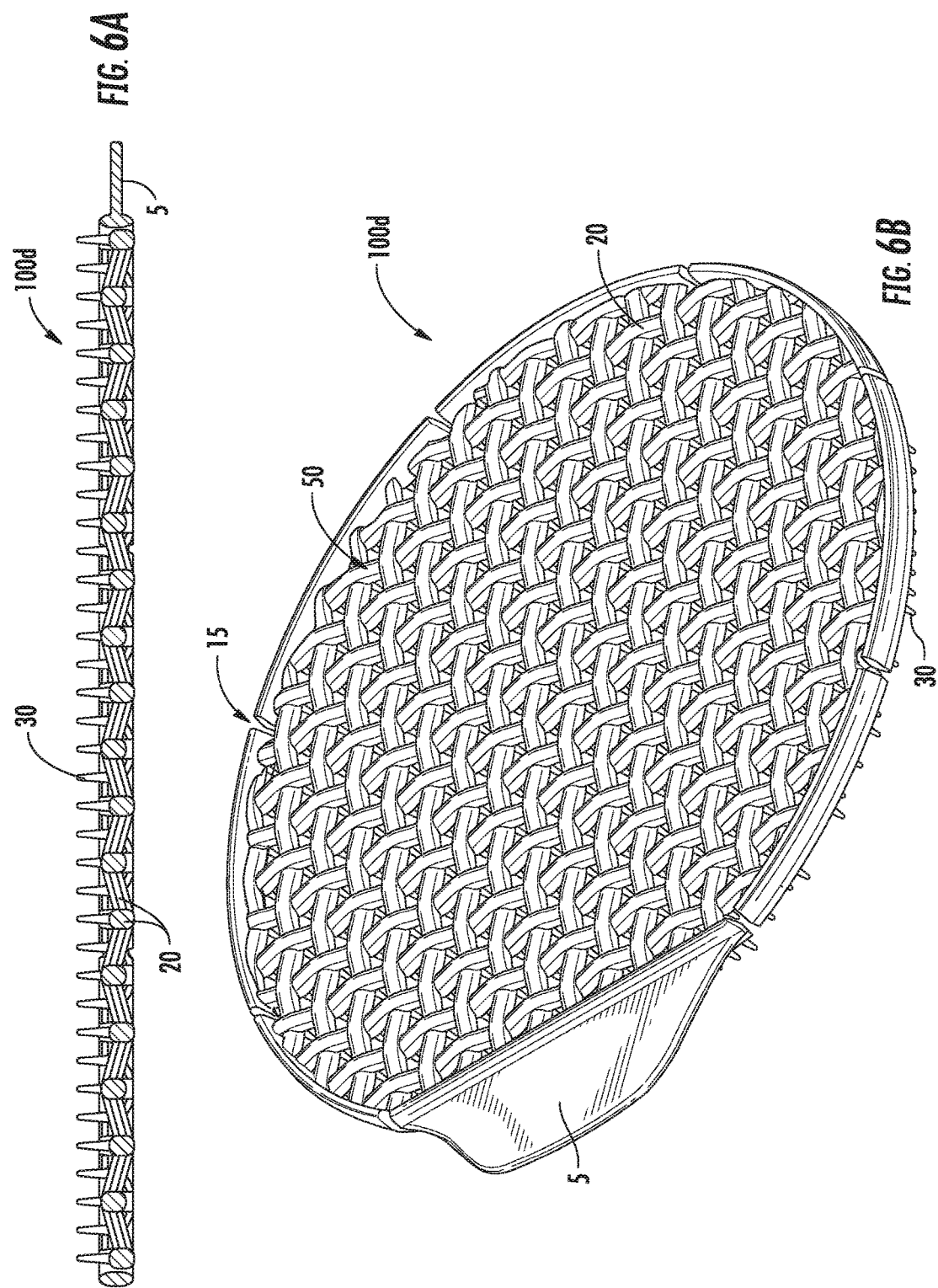

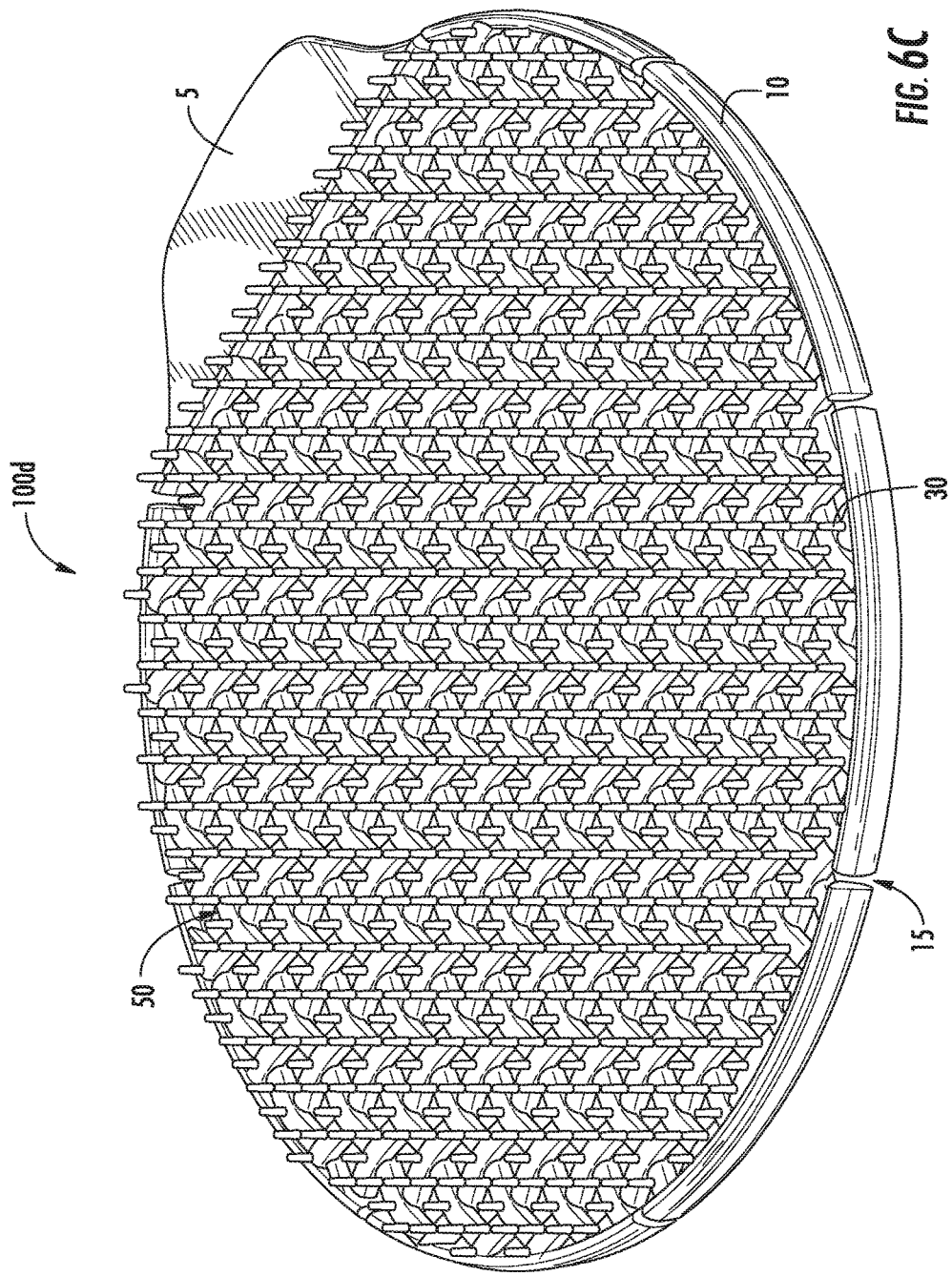

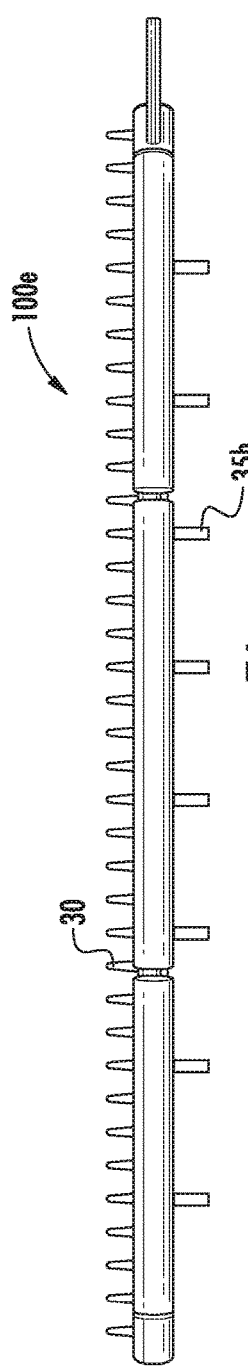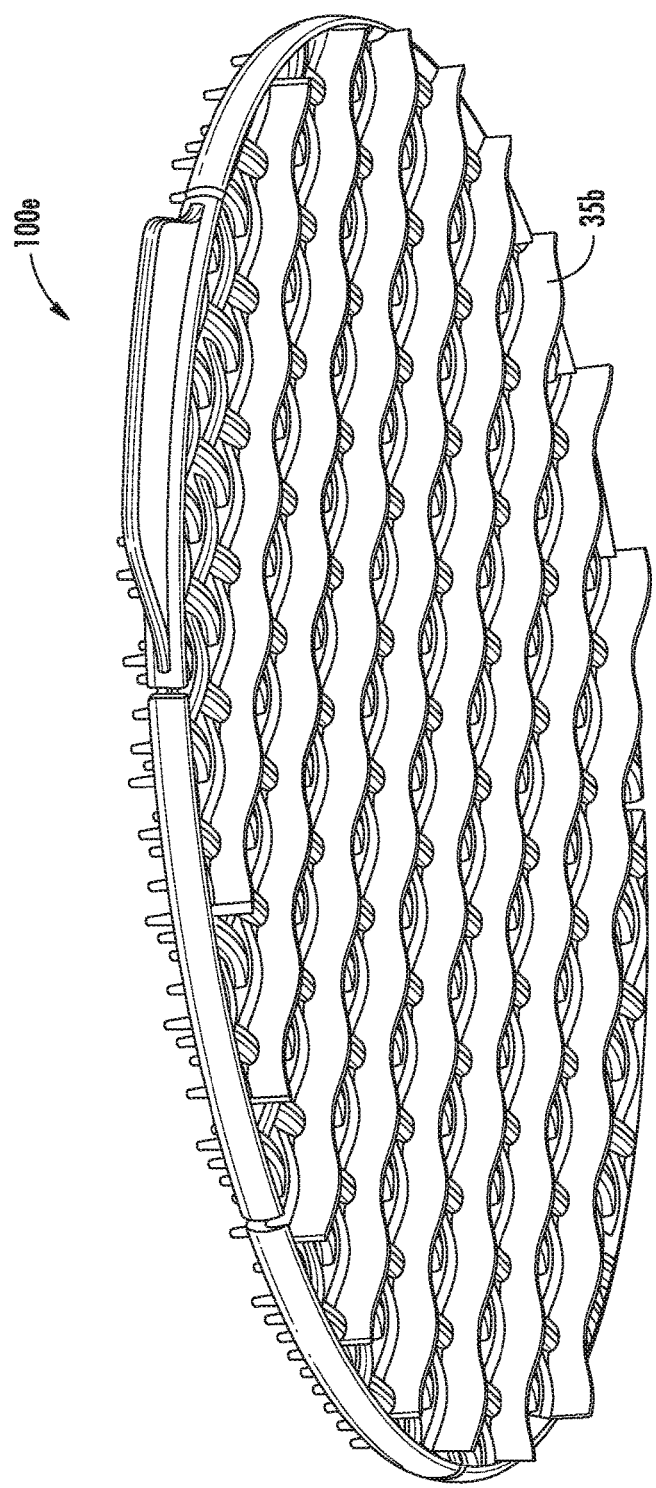

URINAL SCREENS

CROSS-REFERENCE TO RELATED APPLICATIONS

This application claims priority to U.S. Provisional Application No. 62/237,276, filed on Oct. 5, 2015, which is incorporated by reference herein.

BACKGROUND

When a fluid stream is incident upon a urinal, the interaction of the fluid stream and the urinal may cause some of the fluid to splash back toward the user of the urinal. This may cause the user's pants to be splashed and/or cause fluid droplets to end up on the restroom floor. Therefore, urinal screens are often used to reduce the splashing of the fluid, such as back toward the user of the urinal. However, many currently available urinal screens do not sufficiently reduce the splash of the fluid incident upon the urinal. Moreover, many currently available urinal screens trap fluid in the urinal, which may lead to an unpleasant odor.

Thus, there is a need for improved urinal screens that provide sufficient splash reduction without trapping fluid within the urinal at a minimal cost.

SUMMARY

In one aspect, urinal screens are provided including an outer ring, a substantially planar web portion bounded by the outer ring and having a first face and an opposed second face, the web portion including a plurality of web strings disposed in a mesh pattern, such that a plurality of open areas are defined between the web strings, and a plurality of posts projecting from the first face of the web portion, wherein portions of the web strings forming the first face of the web portion are substantially rounded in profile.

In another aspect, urinal screens are provided including an outer ring having a first side and an opposed second side, and a substantially planar web portion bounded by the outer ring and having a first face and an opposed second face, the web portion including a plurality of web strings disposed in a mesh pattern, such that a plurality of open areas are defined between the web strings. The urinal screen has a urine receiving face and an opposed urinal contacting face, the urine receiving face including the first side of the outer ring and the first face of the web portion and the web strings forming the first face of the web portion are substantially rounded in profile and the first side of the outer ring is substantially rounded in profile.

In still other aspects, urinal screens are provided that include various configurations or open areas and posts configured for splash reduction.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

FIGS. 5A, 5B, 5C, 5D, and 5E are a cross-sectional view, lower perspective, top view, bottom view, and upper perspective, respectively, of an embodiment of a urinal screen, in accordance with the present disclosure.

FIGS. 6A, 6B, 6C, 6D, and 6E are a cross-sectional view, lower perspective, upper perspective, bottom view, top view, respectively, of an embodiment of a urinal screen, in accordance with the present disclosure.

FIGS. 7A and 7B are a side view and a lower perspective view, respectively, of an embodiment of a urinal screen, in accordance with the present disclosure.

DETAILED DESCRIPTION

The present disclosure provides urinal screens for screening foreign particles from entering the urinal drain, optionally providing a fragrance or other air freshening substance at the point of use, and reducing the splash from a fluid stream generally directed toward the urinal drain. Various aspects of the present disclosure provide urinal screens and associated methods. In one aspect of the present invention, a urinal screen for reduced splash back is provided.

Figure 1:
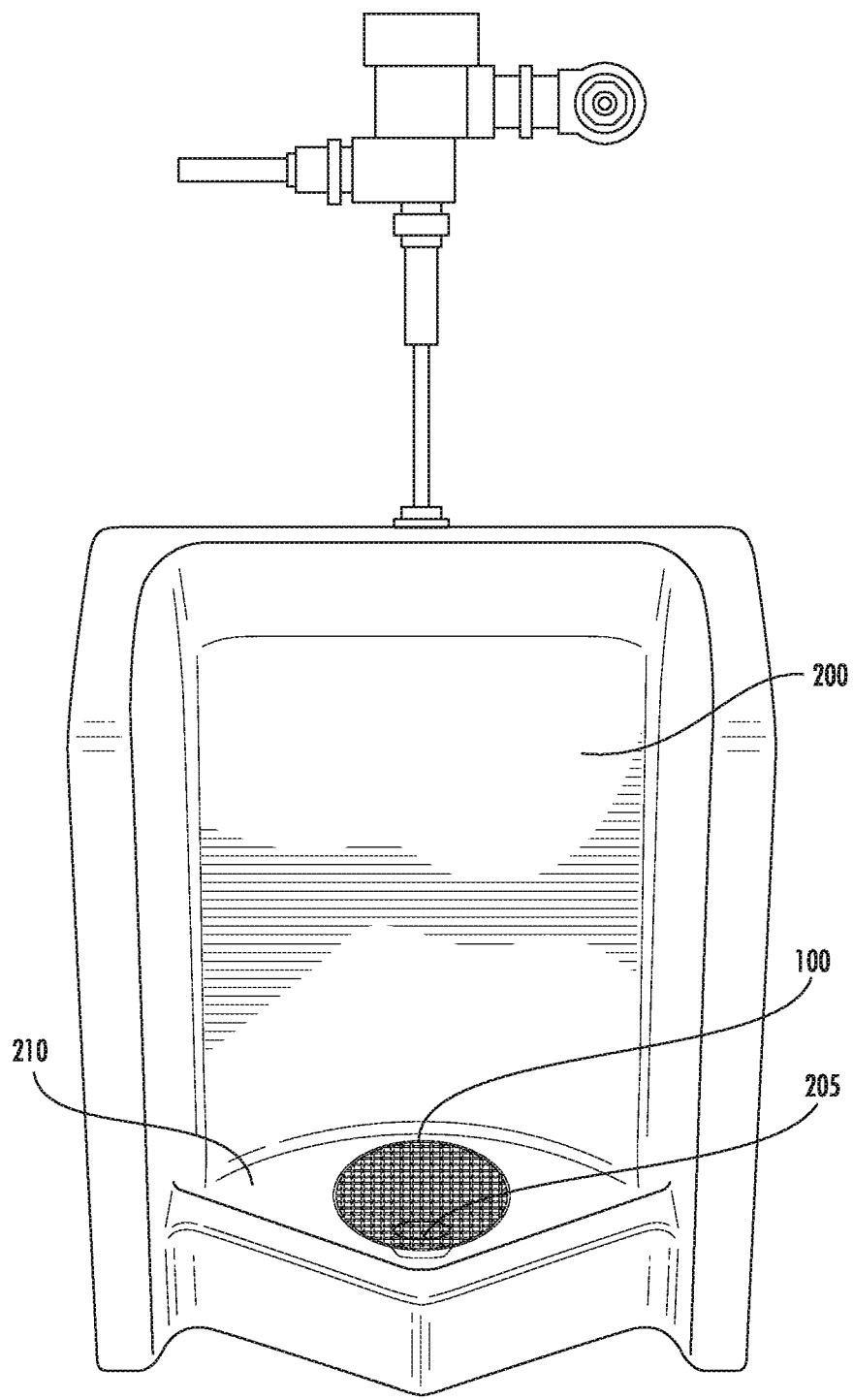
FIG. 1 is a perspective view showing an embodiment of a urinal screen in a urinal, in accordance with the present disclosure.

FIG. 1 illustrates a urinal screen 100 positioned within a urinal 200 in accordance with the present disclosure. In the depicted embodiment, the urinal screen 100 is positioned on the urinal floor 210 and covers the urinal drain 205. For example, a restroom attendant or maintenance crew member may place a urinal screen 100 in a urinal 200 such that the urinal screen 100 generally covers the urinal drain 205. In various embodiments, the urinal screen 100 may be positioned such that a fluid stream generally directed toward the urinal floor 210 and/or the urinal drain 205 may be at least partially incident upon the urinal screen 100. In various embodiments, the urinal screen 100 may be flexible such that the urinal screen may flex and conform to the geometry of the urinal floor 210. Moreover, the urinal screen 100 may have a minimalist design, providing a high performance, light weight, and cost efficient urinal screen.

The urinal screen may, in some embodiments, be further configured to funnel the fluid of the fluid stream into the urinal drain 205 without trapping fluid. Moreover, in various embodiments, the urinal screen 100 may be configured to prevent foreign materials (e.g., gum, cigarette butts, other trash) from entering the urinal drain 205, possibly causing the urinal drain 205 to become clogged. As such, the urinal screen 100 may include a web portion configured to allow fluid to flow through the urinal screen 100 while preventing foreign materials that are large with respect to the web portion from entering the urinal drain 205.

In various embodiments, the urinal screen 100 may be further configured to mask or prevent unpleasant odor. For example, the urinal screen 100 may be configured to prevent fluid from being trapped within the urinal 200. In various embodiments, the urinal screen 100 may be impregnated with a fragrance or other air freshening substance to be released over time.

In various embodiments, the urinal screen 100 may be configured to reduce splashing of the fluid stream incident thereon. For example, the urinal screen 100 may be configured to reduce the amount of fluid that is splashed back away from the urinal floor, out of the urinal, and/or the like from an incident fluid stream. In various embodiments, the urinal screen 100 may be configured to diffuse, deflect, and/or the like the fluid stream incident thereon. For example, the urinal screen 100 may have a reduced area of (e.g., may not have any) surfaces that are substantially flat to the user's view (i.e., in plan view) such that any fluid droplets that may splash off of the urinal screen 100 are not directed back toward the user. For example, the urinal screen 100 may be configured to deflect portions of the fluid stream incident thereon into urinal 200.

For example, it has been discovered that splash back may be reduced by providing a urine receiving face of the urinal screen that has a reduced amount of flat surfaces for an impinging stream of urine to contact. That is, the urinal screens of the present disclosure may include surfaces having a rounded profile on a face of the urinal screen configured to receive urine during use. In some embodiments, alone or in combination with reduction of flat surfaces of the urinal screen, splash reduction also may be achieved by the inclusion of a plurality of posts that project upward from the urine receiving face of the urinal screen and serve to absorb some of the momentum of a splashed fluid stream and redirect the fluid back toward the urinal floor. Various embodiments of urinal screens having these features are described herein; however, it should be understood that embodiments of the disclosure may include only some of the described features or combinations of these features not explicitly described herein.

Figure 2:
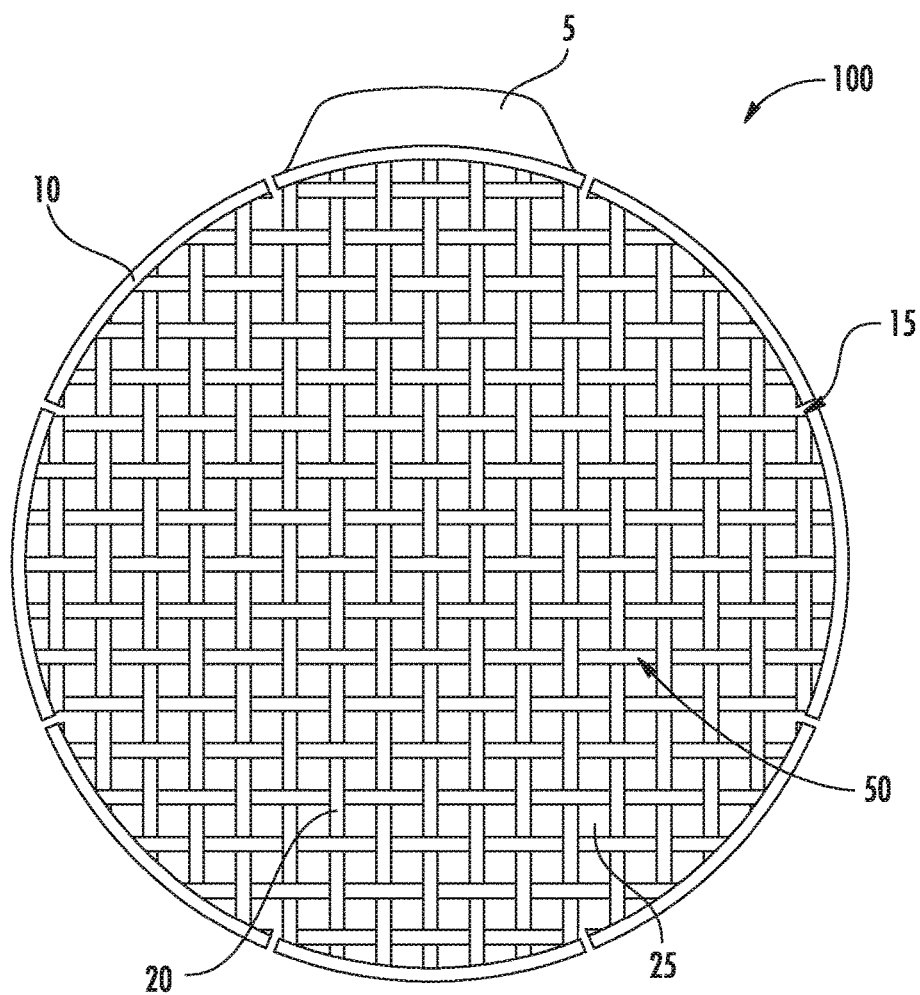
FIG. 2 is a top plan view of an embodiment of a urinal screen, in accordance with the present disclosure.

In certain embodiments, as shown in FIG. 2, a urinal screen 100 includes an outer ring 10 and a substantially planar web portion 50 bounded by the outer ring 10. The web portion has a first face (e.g., a urine receiving face) and an opposed second face (e.g., a urinal contacting or fronting face) and if formed from a plurality of web strings 20 disposed in a mesh pattern, such that a plurality of open areas 25 are defined between the web strings 20. As used herein, the phrase "outer ring" refers to the peripheral rim of the urinal screen that provides structural support for the web portion it bounds. The ring may be any suitable size and shape, such as substantially circular, elliptical, square, rectangular, polygonal, irregular, or novelty shaped. In some embodiments, the outer ring 10 may include a tab 5 that may be configured to act as a handle, labelling area, or the like.

As used herein, the phrase "web strings" refers to elongated cross-members or strands that form the mesh screen of the web portion of the urinal screen. The web strings may have any suitable size and cross-sectional shape, including circular or elliptical.

As used herein, the phrase "substantially planar," when used to describe the web portion, refers to the web portion having a generally flat shape or lying in a two-dimensional plane. That is, the web portion is generally not dome or otherwise three-dimensionally shaped. However, as will be described in greater detail, the web portion may have a woven or faux-woven design, such that the web portion is generally two-dimensional, but has a slight three-dimensional character. Such woven and faux-woven web portions should be understood to be substantially planar within the scope of this disclosure.

As used herein, the phrase "mesh pattern" refers to the web strings of the web portion being arranged in an interwoven or intertwined configuration forming open spaces between the strings, such as a net configuration. The terms "mesh" and "woven" refer to the appearance and properties of the web strings, but not mean that the web strings are in all embodiments separate, overlapping structures. On the contrary, the web strings may be integrally formed, such as by a molding process.

In some embodiments, at least the portions of the web strings forming the urine receiving face of the web portion are substantially rounded in profile. As used herein, the term "rounded in profile" refers to the relevant surface having a curved, non-flat contour. For example, such rounded surfaces may be configured to receive a downward stream of urine such that the impinging stream does not contact a flat surface and the resulting splash is minimized.

FIGS. 2, 3A-3G, 4A-4C, 5A-5E, 6A-6E, 7A-7B, 8, 13A-13D, and 14A-14D provide various views of a urinal screen 100 (embodiments of the urinal screen are labelled 100a through 100h, and referred to collectively herein as "100") in accordance with various embodiments of the present disclosure. In the illustrated embodiments, the urinal screen 100 is generally circular. However, other shapes may be used. For example, the urinal screen 100 may be generally elliptical, square, rectangular, polygonal, irregular, or novelty shaped. For example, the urinal screen 100 may be shaped like a fish or other animal in order to hold the attention of younger users. In general, urinal screen 100 may be sized appropriately to cover the urinal drain 205 and at least a portion of the urinal floor 210. For example, the urinal screen 100 may be approximately four to eight inches across (e.g., in diameter). For example, in one embodiment, the urinal screen 100 is from about 3 inches to about 8 inches in diameter. For example, the urinal screen 100 may be from about 6 inches to about 7 inches in diameter. For example, the urinal screen 100 may be from about three inches to about five inches in diameter.

In various embodiments, the urinal screen 100 includes an outer ring 10. The outer ring 10 is configured to provide structural support for the urinal screen 100. In various embodiments, the outer ring 10 may be elliptical or round in cross-section. In various embodiments, the outer ring 10 may include outer ring gaps 15. The outer ring gaps 15 may be small breaks in the outer ring (e.g., 1 mm to 1 cm in length). In various embodiments, the outer ring gaps 15 may be configured to allow the outer ring 10 to provide structural support for the urinal screen 100 while allowing the outer ring 10 to be flexible enough to conform to a generally arbitrary geometry of a urinal floor 210. In some embodiments, the outer ring 10 may include a tab 5 that may be configured to act as a handle or the like. For example, the tab 5 may act as a billboard and provide information identifying the manufacturer and/or providing manufacturer contact information.

In various embodiments, the urinal screen 100 includes a web portion 50. The web portion 50 includes a plurality of web strings 20. The web strings 20 may be woven or have a woven or semi-woven appearance. For example, as evident from the cross-sectional view of FIG. 3A, the web strings 20 may appear to be woven over and under each other as the warp and weft of a plain weaving. That is, the mesh pattern of the web portion 50 may be a plain weave pattern or other suitable weave pattern. In certain embodiments, the web strings 20 have a wavy shape and intersect orthogonally in a way that makes the web strings appear to be woven together.

In this manner, the web strings 20 are not flat from the perspective of the urinal user (i.e., in plan view). For example, the outer ring 10 defines an imaginary flat, two dimensional plane. Each web string 20 is at an angle with respect to the imaginary plane. Thus, the web portion 50 is inherently three-dimensional, though, as described above should be understood as substantially planar. Moreover, the angle between the imaginary plane and each web string 20 changes constantly along the length of the web string 20. For example, at two nearby points along a web string or adjacent web strings, the gradient fields at the two points will be different. In various embodiments, the web strings 20 may be round (e.g., circular or elliptical) in cross-section. Thus, in certain embodiments, the web portion 50 may be configured such that there are no shoulders, flat surfaces, or inside corners off of which a fluid stream may splash. Moreover, such a design encourages flow of the urine toward the urinal drain without significant splash back.

The web strings 20 may be arranged (e.g., woven) in such a way as to provide open areas (e.g., holes or apertures) 25 in the web portion 50 configured to allow the fluid of the fluid stream to pass through the urinal screen 100. However, the open areas 25 may be configured to be small enough to not allow large foreign items to enter the urinal drain 205.

In certain embodiments, as shown in FIGS. 13A-13D and 14A-14D, the urinal screen 100h/100i includes a flat disc 40 instead of a web portion. Specifically, the urinal screen 100h/100i includes a disc 40 having a plurality of holes 25 therethrough.

The open areas 25 may have any suitable size and shape. In certain embodiments, the open areas of the web portion have a major dimension of approximately 5 mm to 2 cm. As used herein, the phrase "major dimension" refers to the largest diameter, axis length, or side length of the open area when viewed in plan view. In some embodiments, the open areas of the web portion have a major dimension of from about 1 mm to about 30 mm in plan view. For example, the open areas of the web portion may have a major dimension of from about 5 mm to about 10 mm in plan view. For example, the open areas of the web portion may have a major dimension of from about 5 mm to about 7 mm in plan view. For example, the open areas of the web portion may have a major dimension of about 6.5 mm in plan view.

Figure 5C:
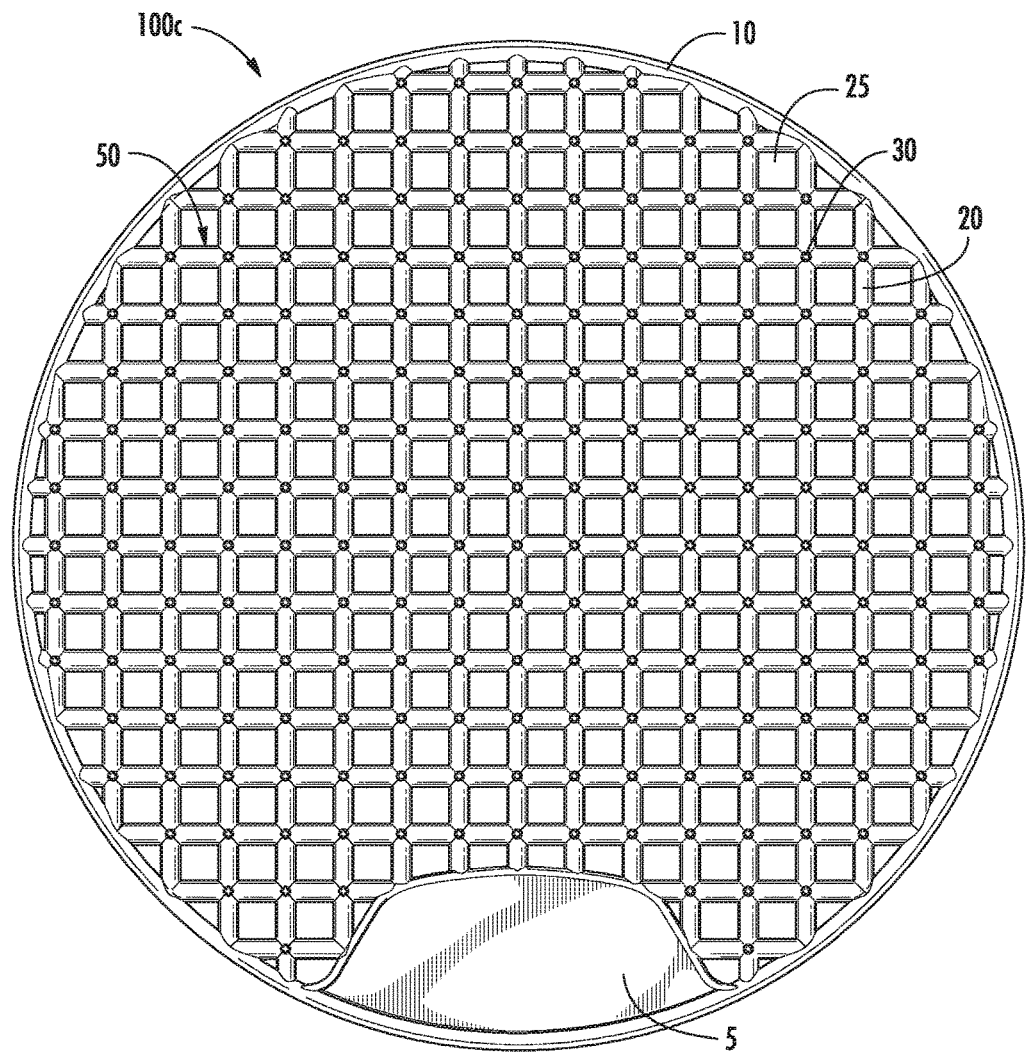
Figure 5D:
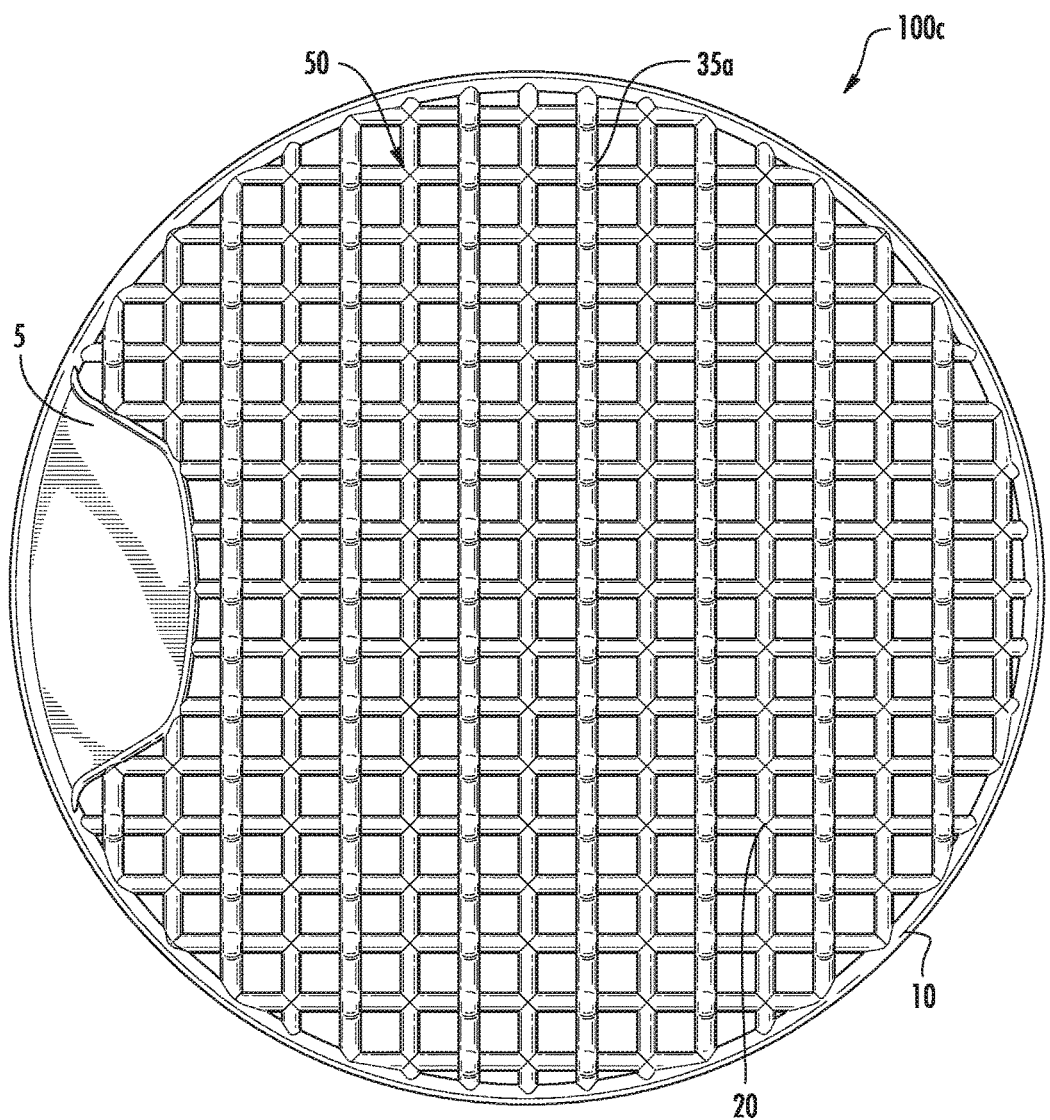
Figure 6D:
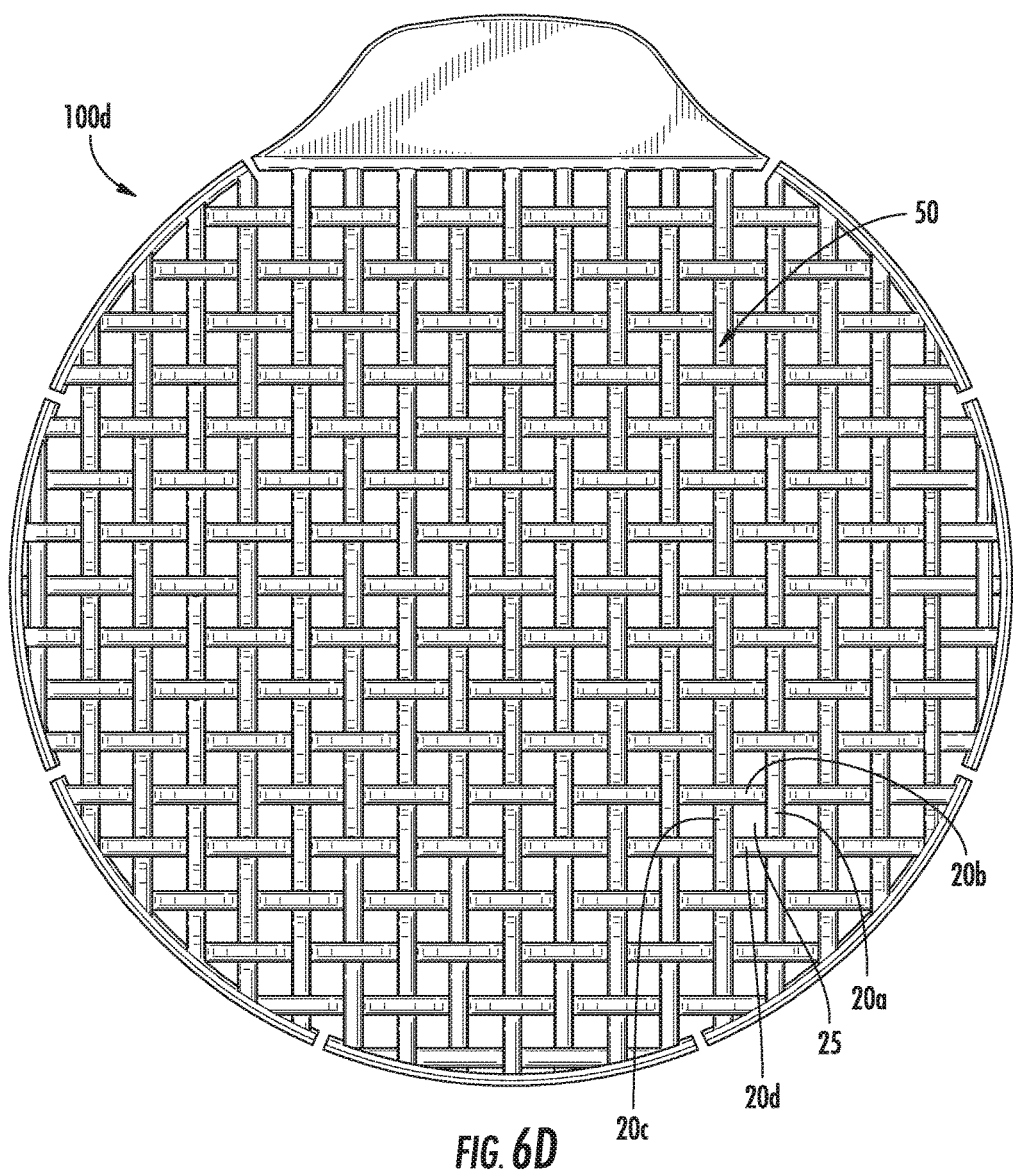
Figure 6E:
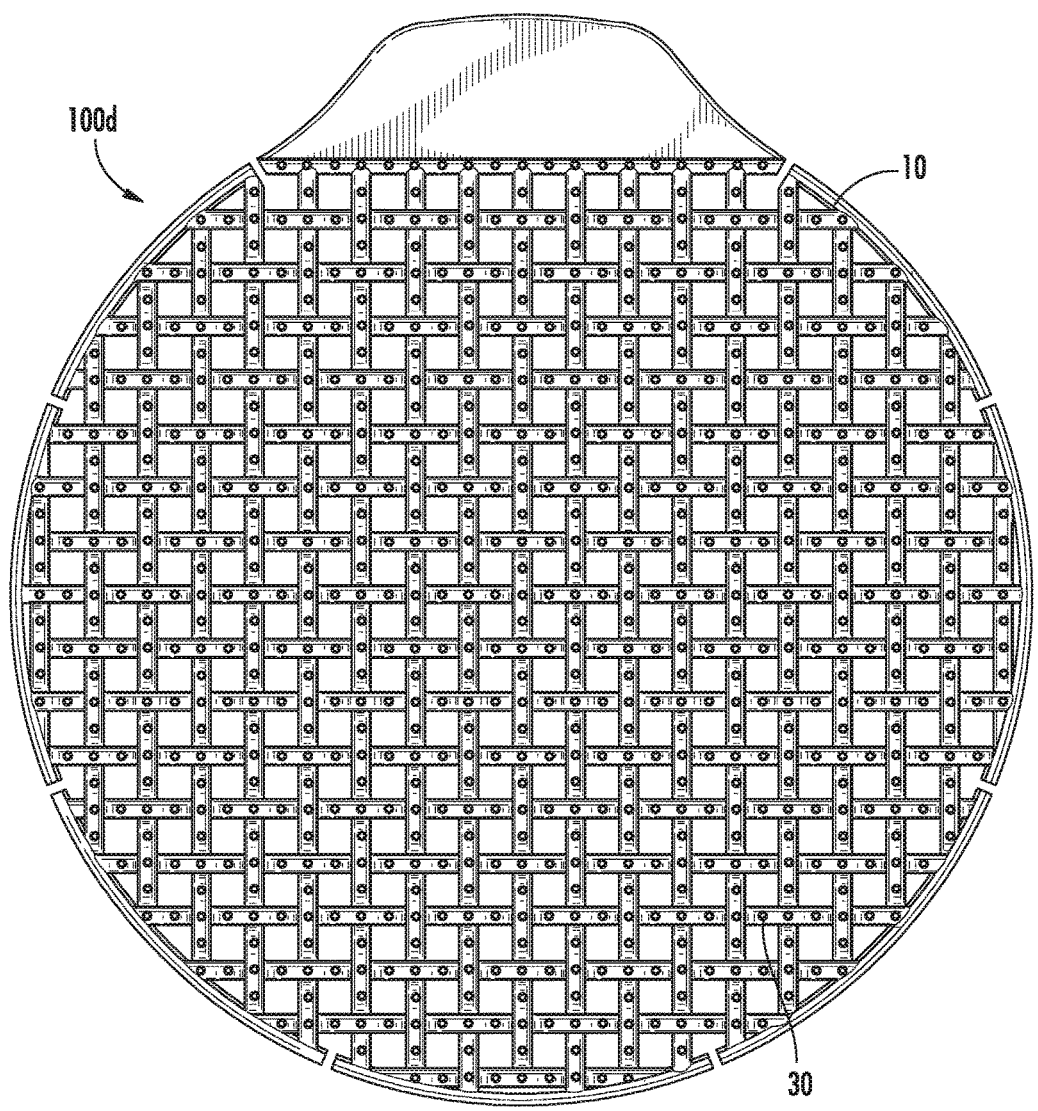
Figure 8:
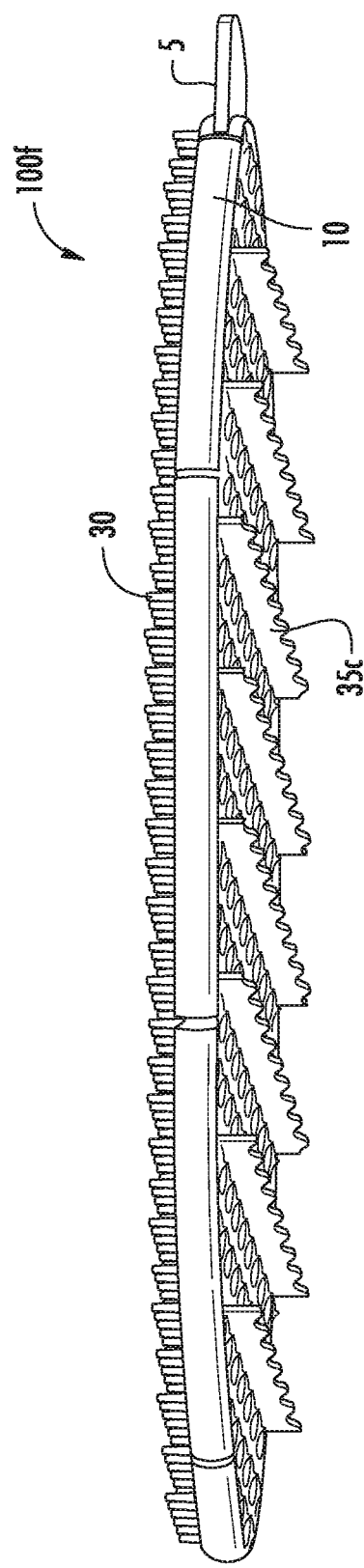
FIG. 8 is a lower perspective view of an embodiment of a urinal screen, in accordance with the present disclosure.
Figure 12:
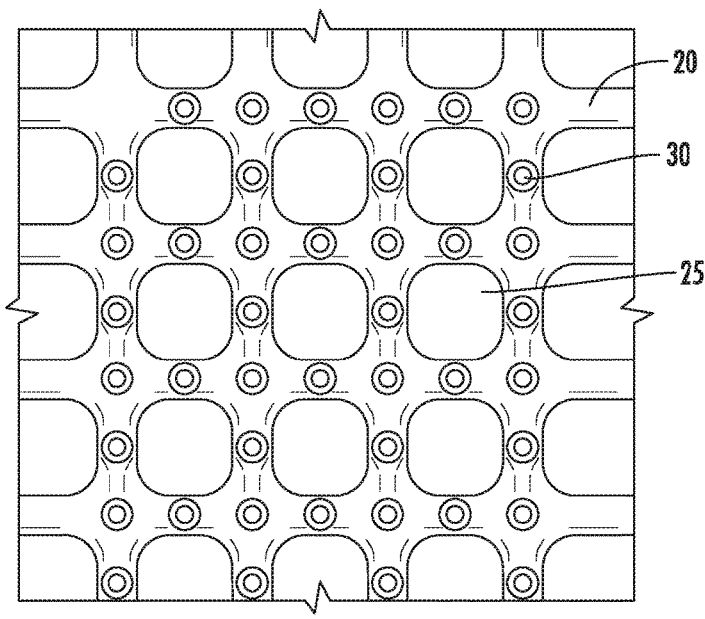
FIG. 12 is a partial top view of a web portion of an embodiment of a urinal screen, in accordance with the present disclosure.
Figure 13A:
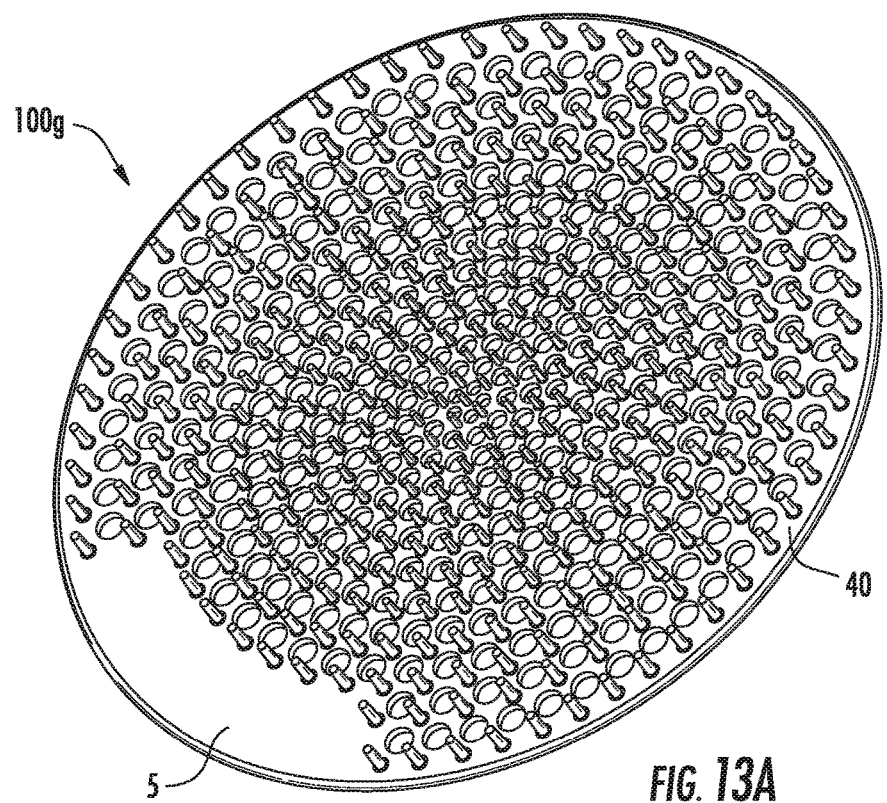
FIGS. 13A, 13B, 13C, and 13D are an upper perspective view, side view, top view, and bottom view, respectively, of an embodiment of a urinal screen, in accordance with the present disclosure.
Figure 13B:
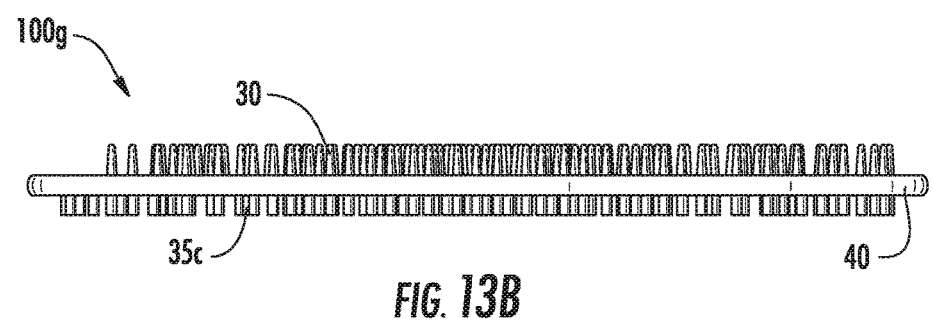
Figure 13C:
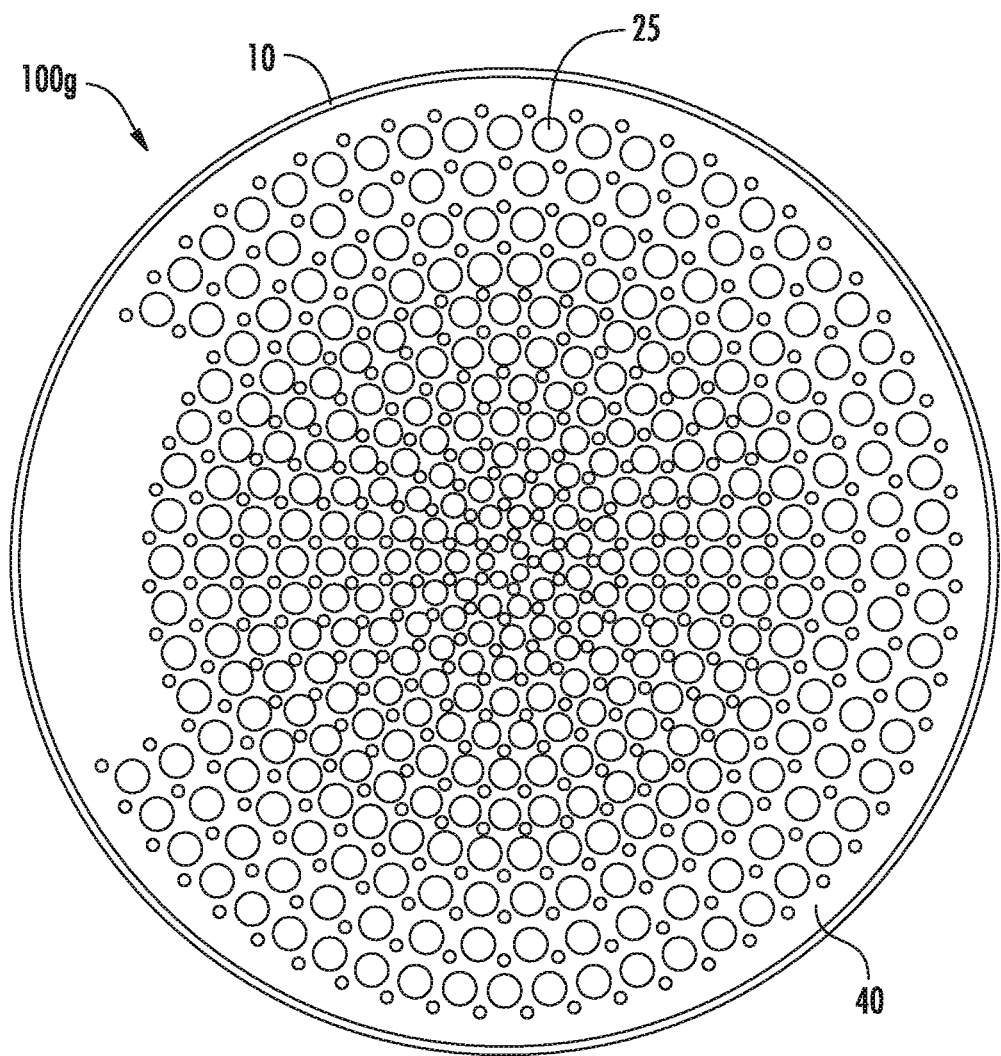
Figure 13D:
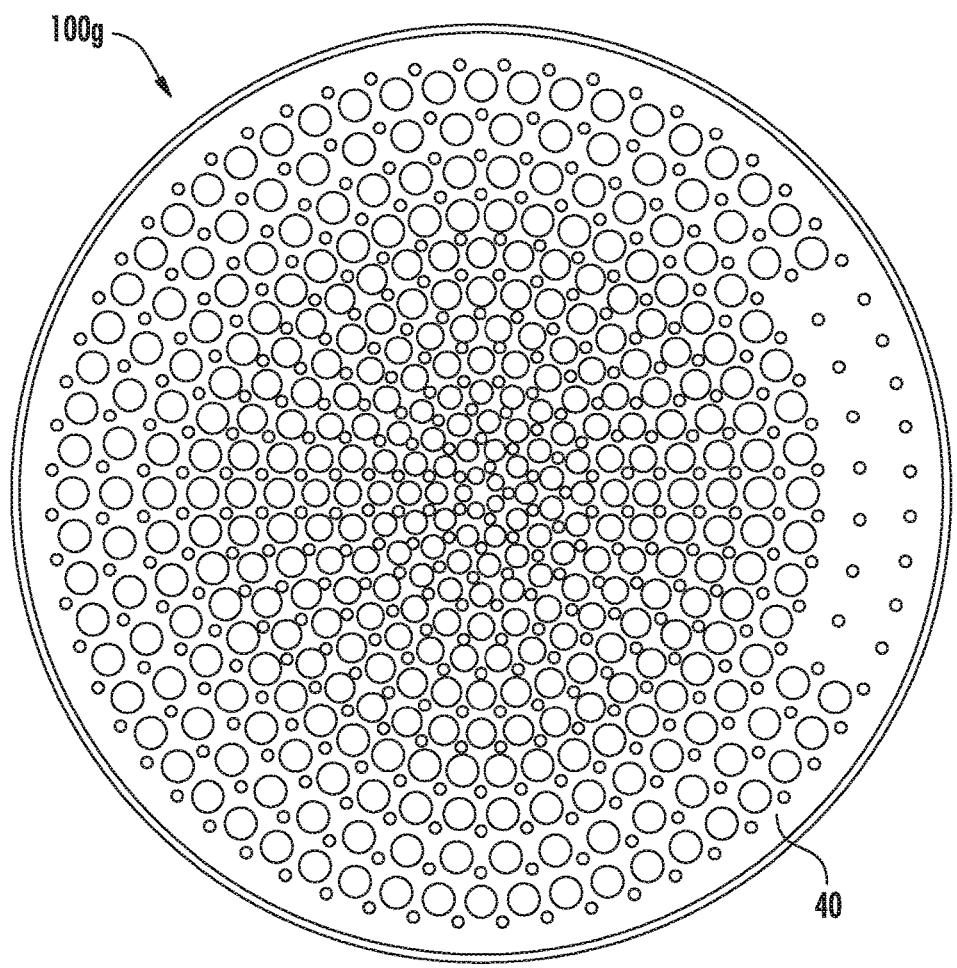
Figure 14A:
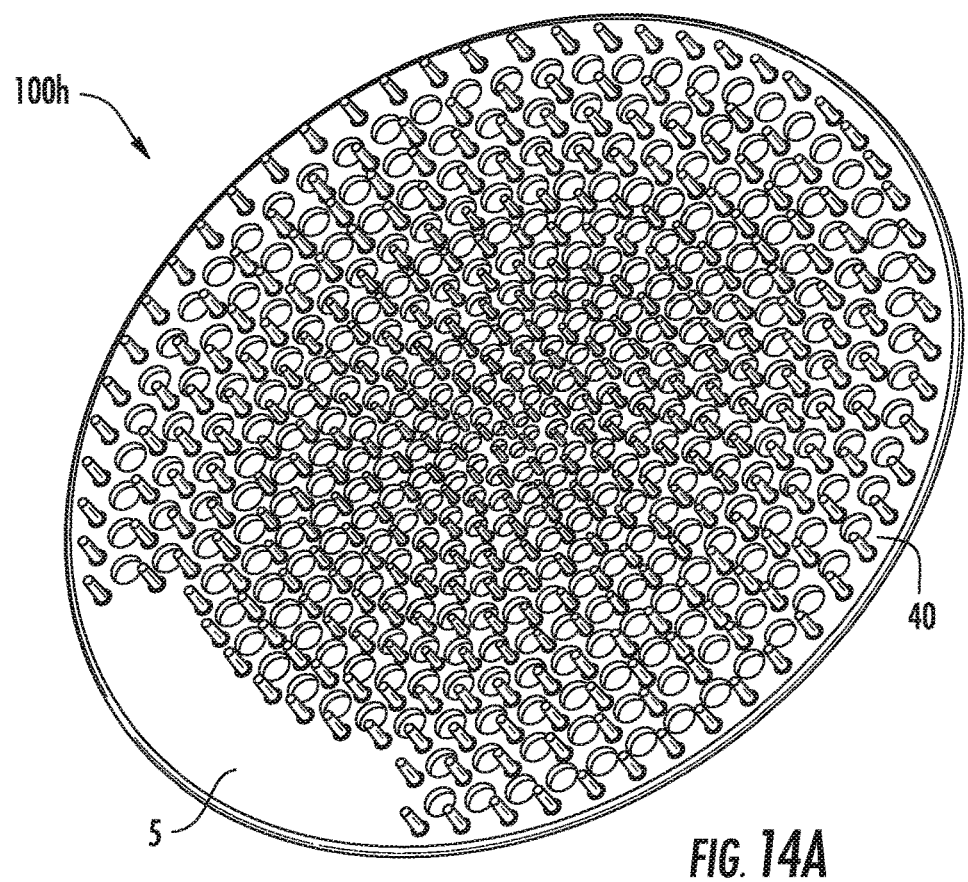
FIGS. 14A, 14B, 14C, and 14D are an upper perspective view, side view, top view, and bottom view, respectively, of an embodiment of a urinal screen, in accordance with the present disclosure.
Figure 14B:
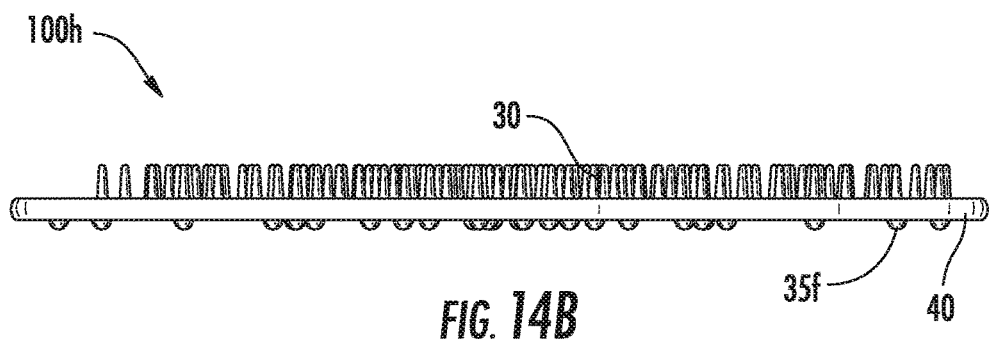
Figure 14C:
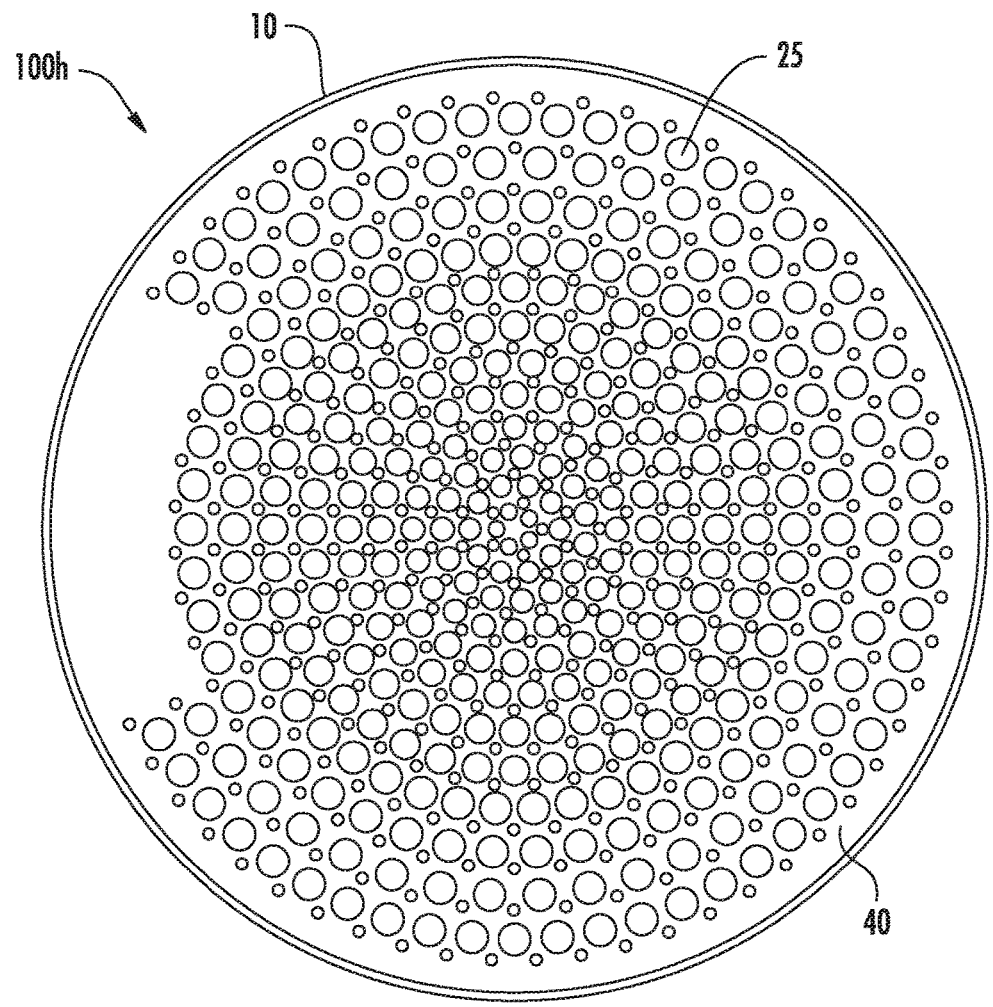
Figure 14D:
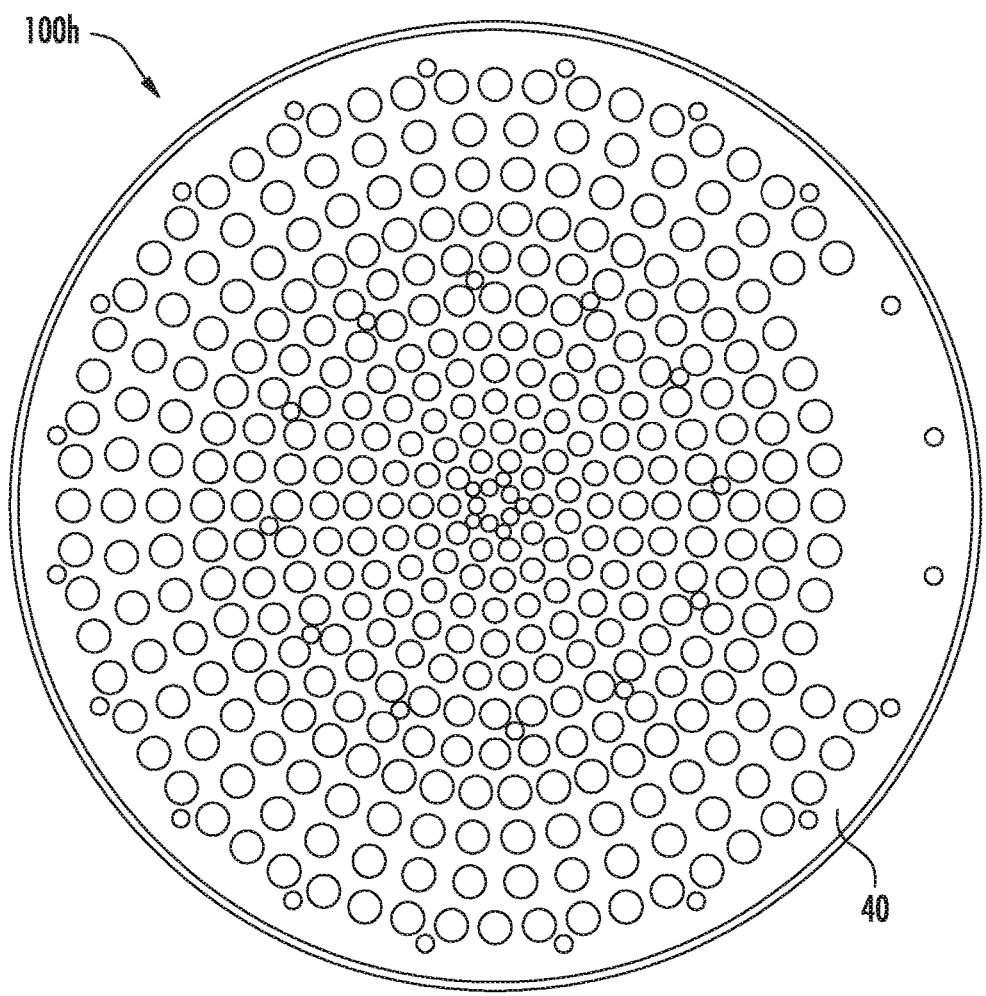

In certain embodiments, as shown in FIGS. 2, 3F, 4A, 5C, and 6D, the open areas 25 may be generally square or rectangular in shape when viewed in plan view. In some embodiments, as shown in FIG. 12, the open areas are polygonal in shape, but have rounded corners. In other embodiments, as shown in FIGS. 13C and 14C, the open areas 25 are circular or elliptical in shape. In certain embodiments, as shown in FIG. 6D, each open area 25 is defined by four web strings (20a, 20b, 20c, 20d). In such embodiments, the open area 25 may be square in shape.

In certain embodiments, when viewed in plan view, the open areas 25 of the urinal screen 100 may occupy from about 25 percent to about 50 percent of the surface area of the urinal screen 100. For example, the open areas 25 of the urinal screen 100 may occupy from about 35 percent to about 45 percent of the surface area of the urinal screen 100. For example, the open areas 25 of the urinal screen 100 may occupy from about 35 percent to about 40 percent of the surface area of the urinal screen 100.

In certain embodiments, as shown in FIG. 6D, the plurality of web strings 20 includes a first set of the web strings 20a, 20c that are substantially parallel to one another and a second set of the web strings 20b, 20d that are substantially parallel to one another and are substantially perpendicular to the first set of web strings 20a, 20c. As mentioned herein, such web strings may be formed in a woven or faux-woven pattern.

Figure 3A:
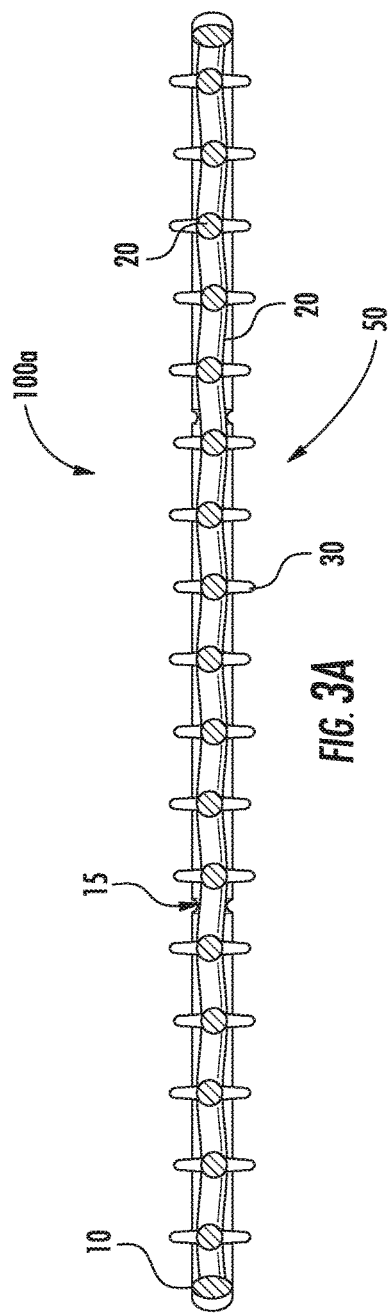
FIGS. 3A, 3B, 3C, 3D, 3E, 3F, and 3G are a cross-sectional view, side view, upper perspective, lower perspective, partial lower perspective, top plan view, and bottom plan view, respectively, of an embodiment of a urinal screen, in accordance with the present disclosure.
Figure 3B:
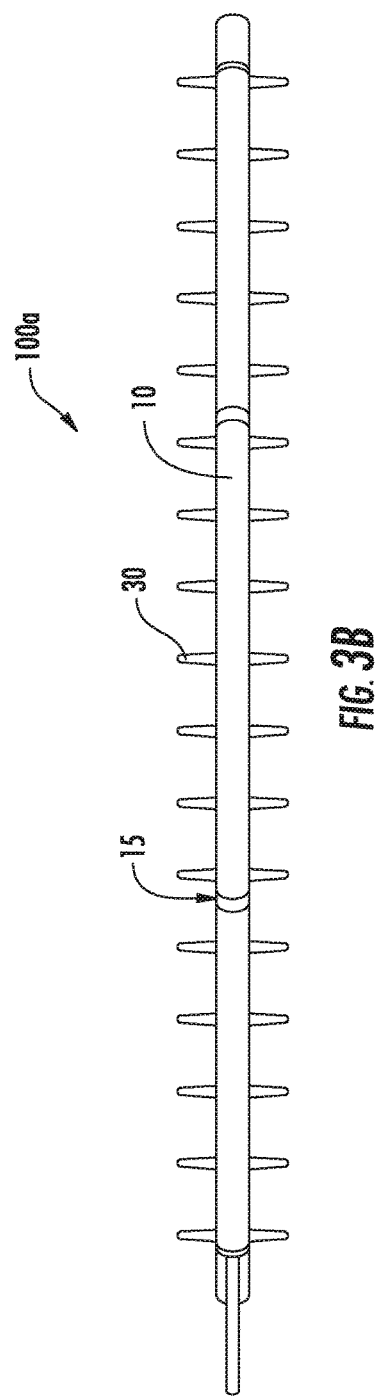
Figure 3D:
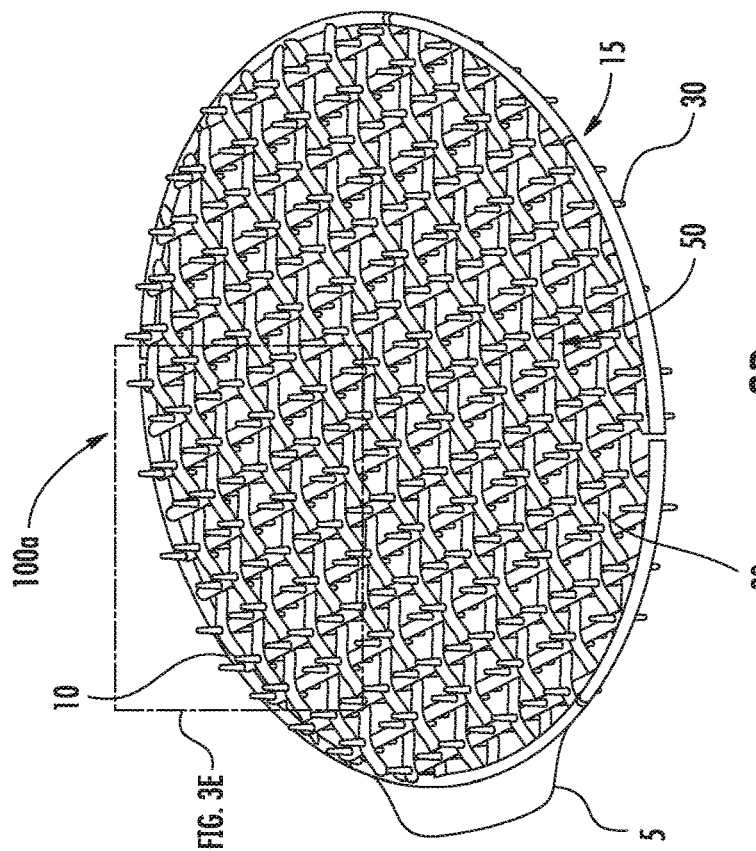
Figure 3C:
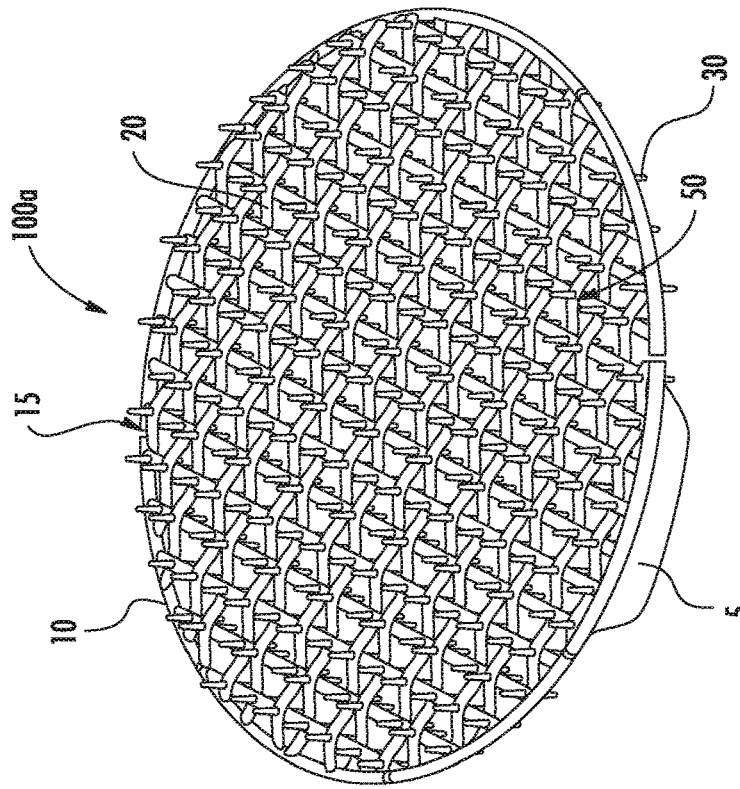
Figure 3E:
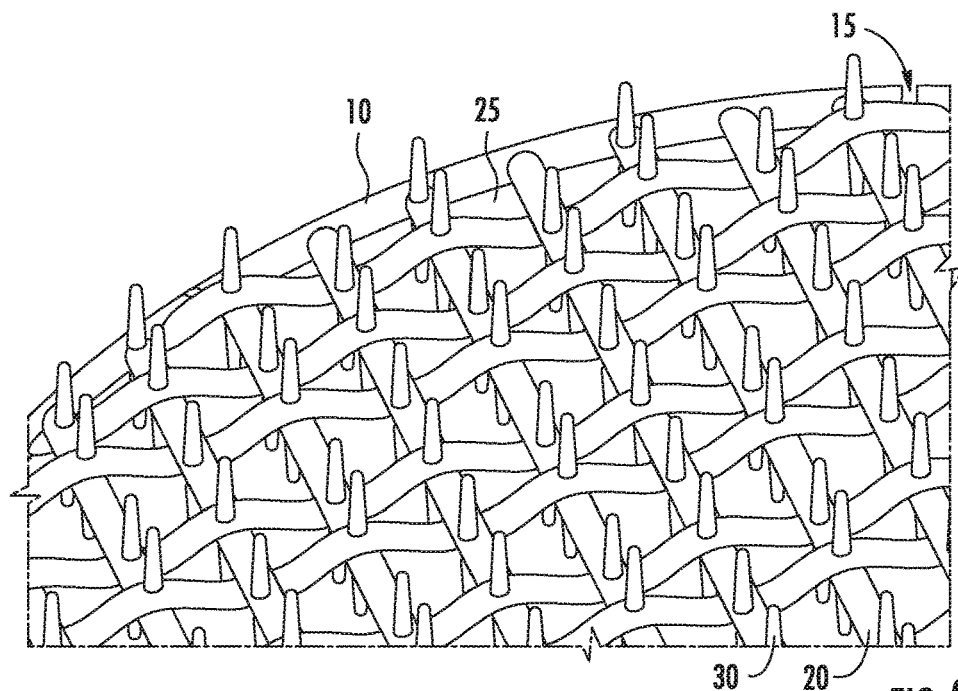
Figure 3F:
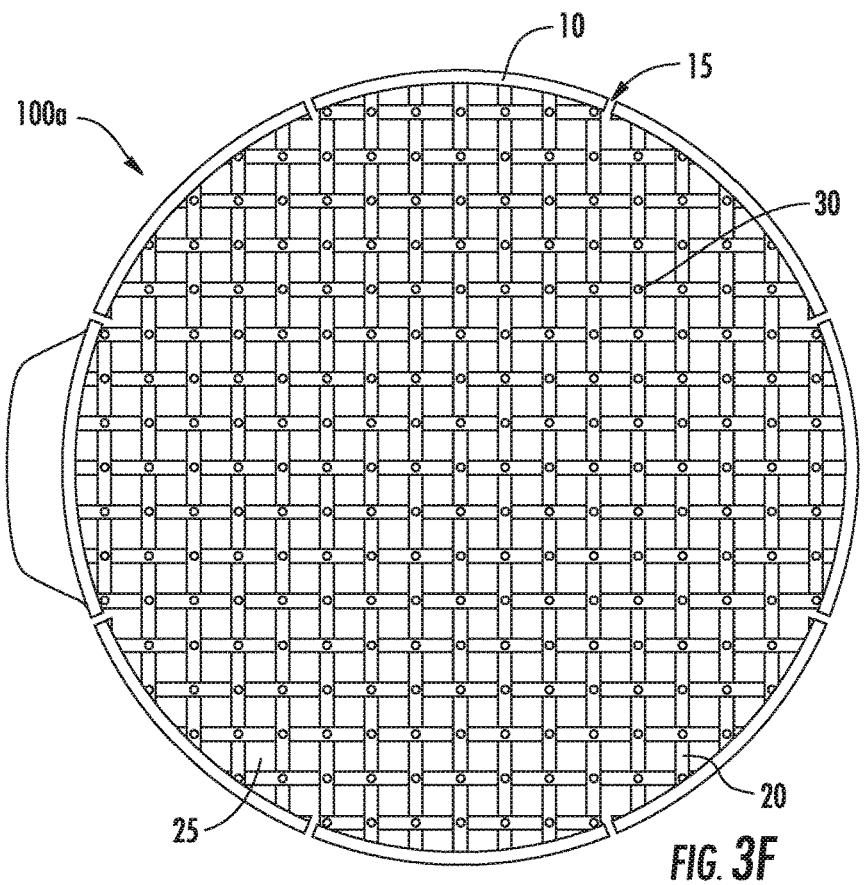
Figure 3G:
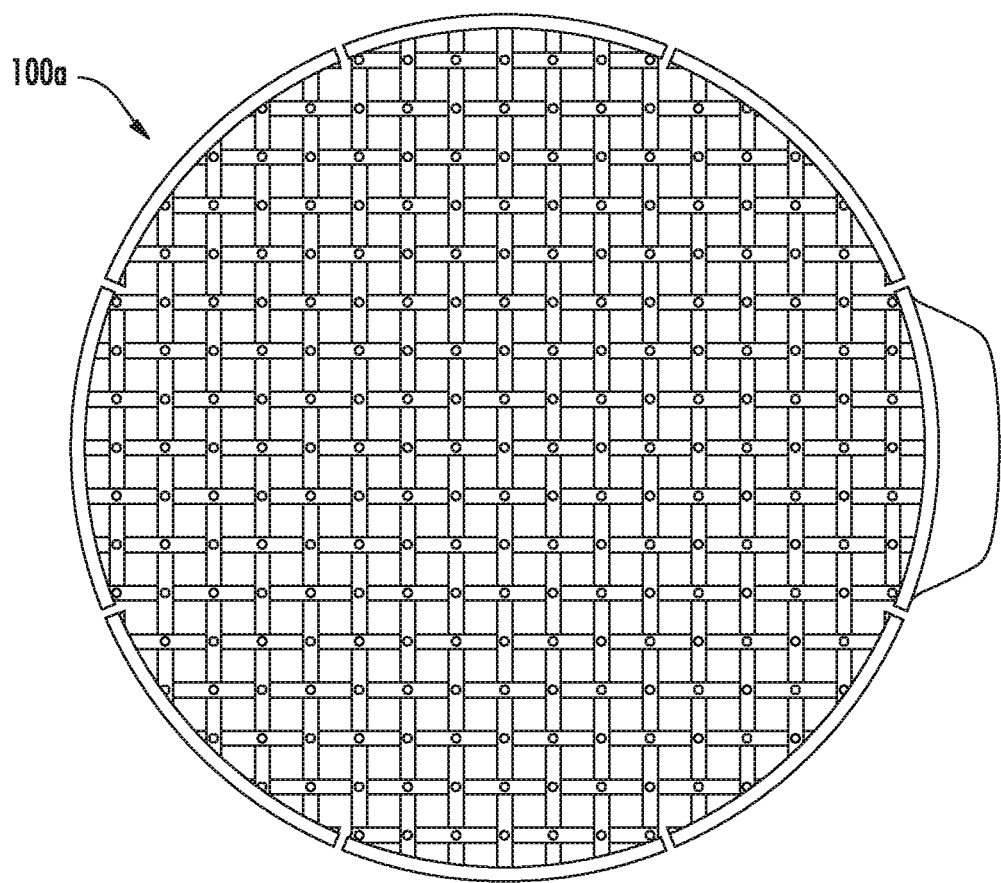

In various embodiments, alone or in combination with the rounded profile web strings of the web portion, a urinal screen 100 may include a plurality of posts 30 projecting from the first face (e.g., the urine receiving face) of the web portion 50. As shown in FIGS. 3A-3G, 4A-4C, 5A-5E, 6A-6A, 7A-7B, 8, 13A-13D, and 14A-14D, the web portion 50 may have a plurality of posts (e.g., nubs, spikes, or grass blades) 30 extending therefrom. For example, a post 30 may be positioned at each node of the web (e.g., where two web strings 20 intersect). In another example, a post 30 may be positioned at the midpoint between each adjacent pair of nodes of the web. As shown in FIG. 3E, in some embodiments, a post 30 may be positioned at each node of the web and at the midpoints between each adjacent pair of nodes of the web. In other embodiments, a variety of post 30 arrangements may be utilized. For example, in one embodiment, there are approximately twenty posts 30 per square inch on each side of the urinal screen 100.

The posts may be of any suitable size and shape. In various embodiments, each post 30 may have a height of between 0.5 mm and 1 cm. For example, in one embodiment, each post is approximately 2.5 mm in height. In various embodiments, each post 30 is the same length. In various embodiments, each post 30 is generally round (e.g., circular or elliptical) in cross-section. In some embodiments, as shown in FIG. 3A, each post 30 has a substantially rounded tip and a substantially rounded profile. That is, both the tip and the body of the post may have surfaces with a curved, non-flat contour.

Figure 9:
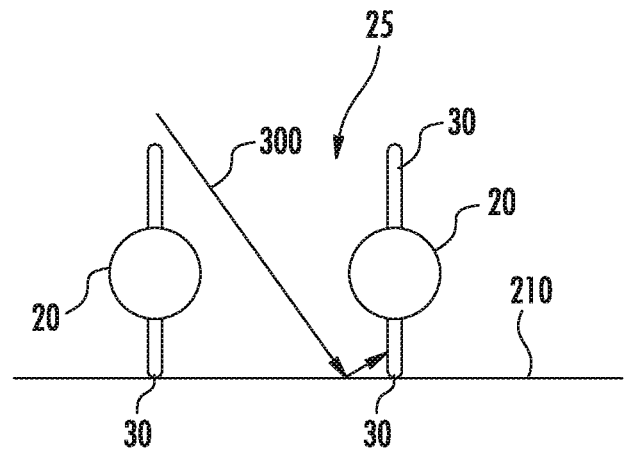
FIG. 9 is a cross-sectional view of a fluid stream interacting with a portion of a urinal screen, in accordance with example embodiments of the present invention.

In various embodiments, the urinal screen is configured to deflect a fluid stream incident thereon into a urinal. FIG. 9 shows an example of a portion of a fluid stream 300 incident upon a portion of a urinal screen 100. A portion of the fluid stream 300 passes through open area 25 and splashes off of the urinal floor 210. The splashed fluid stream 300 is incident upon a post 30, which may absorb some of the momentum of the splashed fluid stream and redirect the fluid back toward the urinal floor 210. Once the fluid has settled onto the urinal floor 210, the fluid may flow freely along the urinal floor 210 into the urinal drain 205. Similarly, if a portion of a fluid stream 300 is incident upon a web string 20 or post 30, the web string 20 or post 30 may deflect the fluid stream 300 through a open area 25 by absorbing at least a portion of the momentum of the fluid stream 300. As the urinal screen 100 does not have any flat surfaces, shoulders, and/or the like, any splashed portion of the fluid stream 300 may be directed such that the splashed portion of the fluid stream further interacts with the urinal screen 100, is directed down toward the urinal floor 210, and/or the like. However, a splashed portion of the fluid stream 300 is not directed back toward the user, due to the geometry of the urinal screen 100.

The outer ring 10 may define a first (e.g., urine receiving) side of the urinal screen 100 and a second (e.g., urinal contacting or fronting) side of the urinal screen 100. In various embodiments, the urinal screen 100 is reversible. For example, as shown in FIGS. 3A-3G, the first side of the urinal screen 100 may have the same pattern of posts 30 as the second side of the urinal screen 100. In such embodiments, the restroom attendant or maintenance crew member that places the urinal screen 100 in the urinal 200 need not worry about placing a particular side of the urinal screen in the up position. Additionally, the posts 30 may hold the urinal screen 100 slightly above the urinal floor 210, allowing fluid to flow freely under the urinal screen 100 into the urinal drain 205.

Thus, in certain embodiments, the second (e.g., urinal contacting) face of the urinal screen includes an elevational feature configured to elevate at least a portion of the web portion off of a urinal floor. That is, the second face of the urinal may be configured to contact the urinal by elevating at least some of the web portion off the floor. For example, the outer ring, a portion of the web portion, or other elevational features may be provided to elevate the web portion. In other embodiments, the urinal contacting face of the urinal screen may be configured such that the web portion contacts the urinal.

Figure 4A:
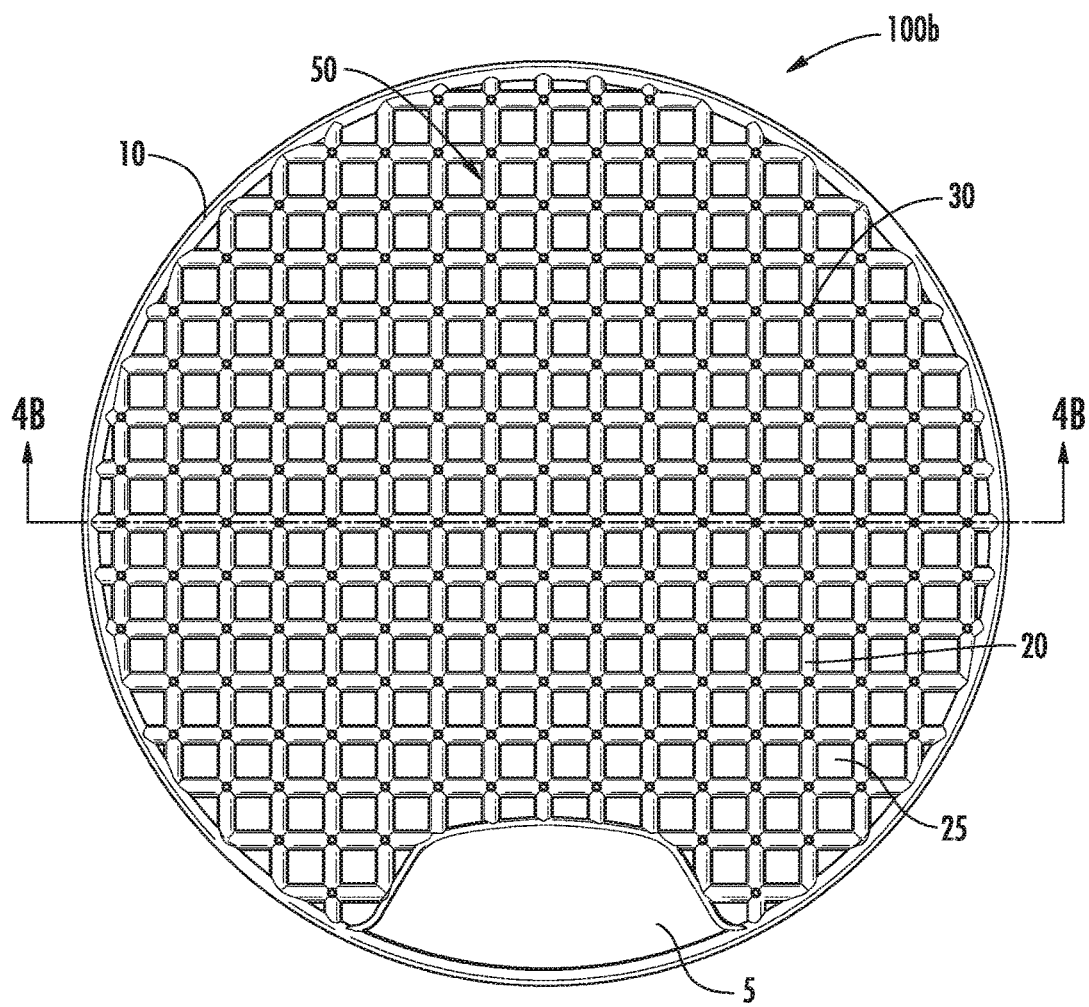
FIGS. 4A, 4B, and 4C are a top view, cross-sectional view, and perspective view, respectively, of an embodiment of a urinal screen, in accordance with the present disclosure.
Figure 4B:
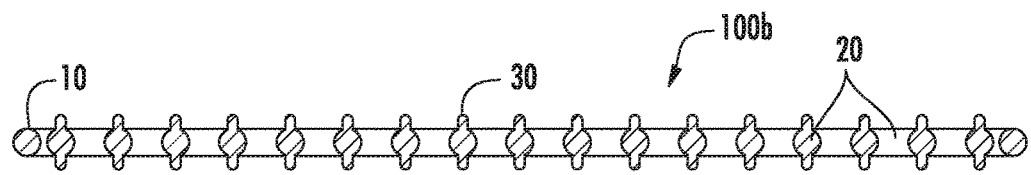
Figure 4C:
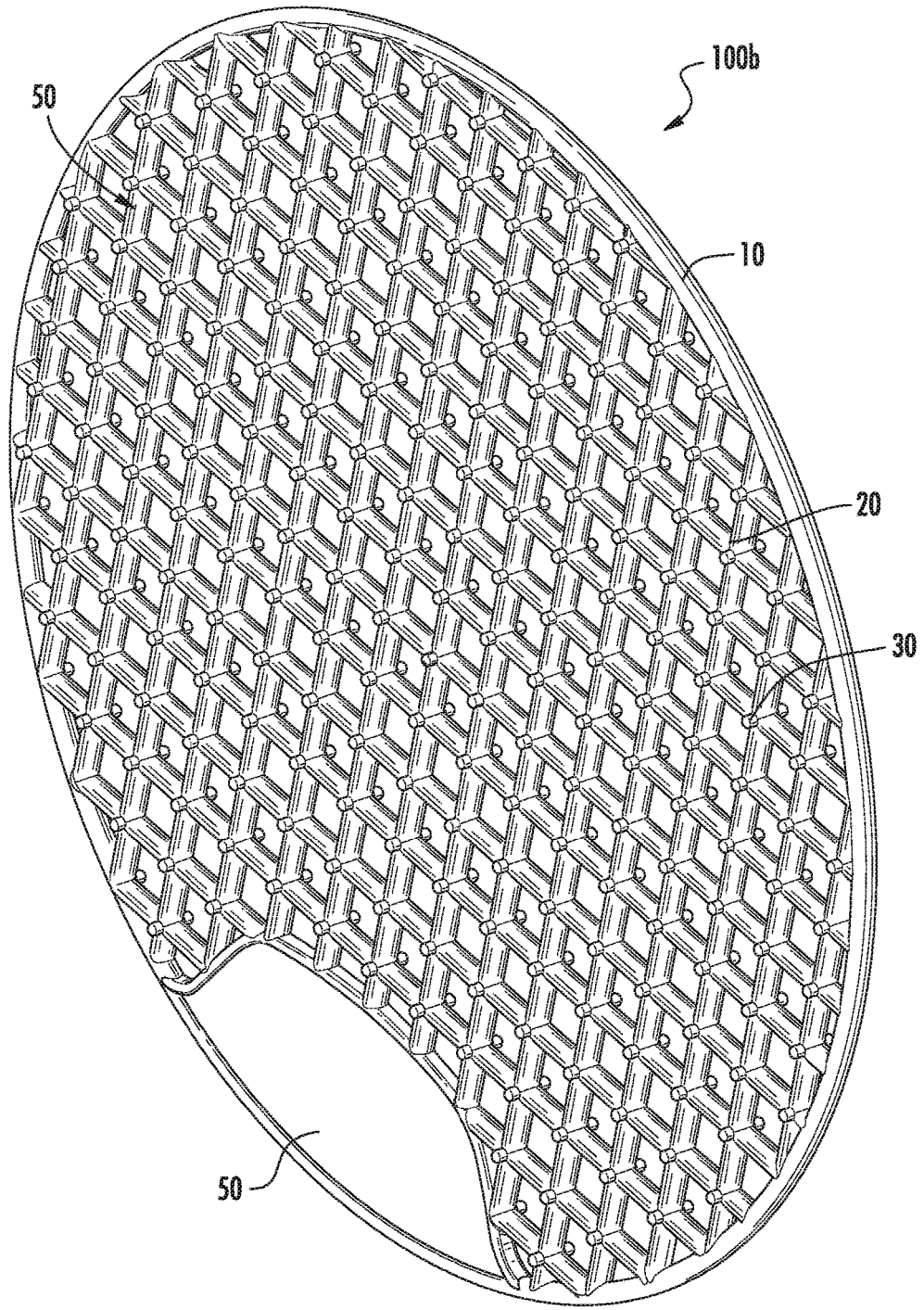
Figure 11:
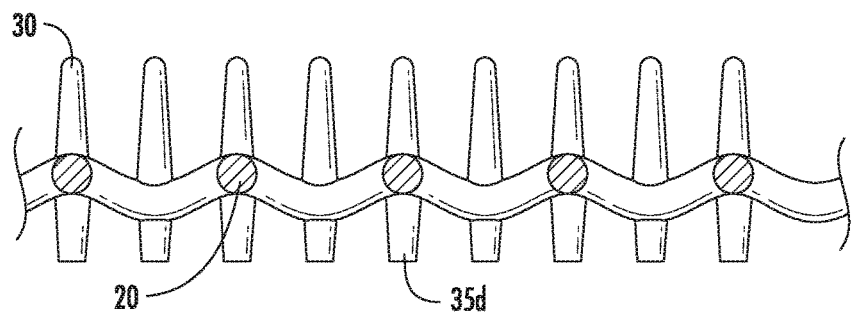
FIG. 11 is a partial cross-sectional view of an embodiment of a urinal screen, in accordance with the present disclosure.

The elevational feature 35 may have a variety of configurations and designs, some of which are illustrated at FIGS. 5A-5D, 7A-7B, 8, 11, 13A-13D, and 14A-14D (embodiments of the elevational feature are labelled 35a through 35f, and referred to collectively herein as "35"). In certain embodiments, the elevational feature includes a plurality of posts or ribs projecting from or integral with the second face of the web. As mentioned herein, and as shown in FIGS. 3A and 4B, the posts of the elevational feature may be the same size and/or pattern as the posts 30 on the urine receiving face of the urinal screen. In other embodiments, as shown in FIGS. 11, 13B, and 14B, the posts of the elevational feature 35 may be a different size, geometry and/or pattern than posts 30 on the urine receiving face of the urinal screen.

Figure 10:
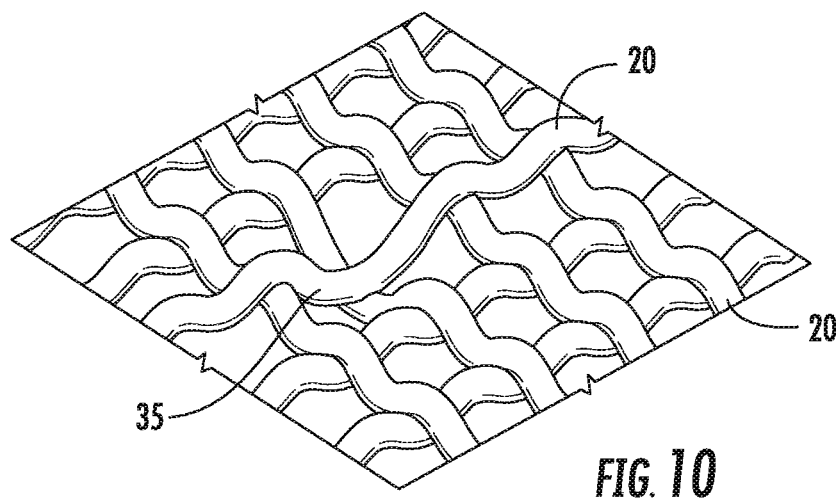
FIG. 10 is a partial perspective view of a web portion of an embodiment of a urinal screen, in accordance with the present disclosure.

In some embodiments, as shown in FIGS. 5A-5D, 7A-7B, 8, the elevational feature 35 includes a plurality of ribs extending from the second face of the web portion. The ribs may have any suitable, size, geometry, and placement. For example, as shown in FIGS. 5A-5B, the undulating ribs of elevational feature 35a may be integral with a portion of web strings 20. In other embodiments, as shown in FIG. 10, an elevational feature 35 may be formed by a portion of the web portion having an exaggerated width relative to the remaining portion of the web portion.

In certain embodiments, the urinal screen 100 is configured to reduce splashing of a fluid stream incident thereon by providing a reduced area of surfaces that are substantially flat to the user's view (i.e., in plan view) such that any fluid droplets that may splash off of the urinal screen 100 are not directed back toward the user. In particular, it has been discovered that splash back may be reduced by providing a urine receiving face of the urinal screen that has a reduced amount of flat surfaces for an impinging stream of urine to contact. In some embodiments, any combination of the outer ring, each of the plurality of web strings, and/or each of the plurality of posts has a generally rounded profile, so as to reduce flat surfaces upon which a stream of urine may be incident.

For example, as compared to current commercial urinal screen offerings, the urinal screens of the present disclosure largely eliminate surfaces that a stream of urine would contact at a roughly 90 degree angle. Most commercial urinal screens include a flat section with features protruding to provide splash reduction. In contrast, embodiments of screens of the present disclosure generally do not have a flat base, and instead have a web portion formed by rounded strands intersecting one another. Because of the rounded shape of the strands, such screens have unique geometric characteristics. For example, every imaginary cross-sectional plane taken parallel to the faces of the urinal screen yields a semi-unique cross-section. That is, because the thickness of the strands is governed by the equation defining a circle, no cross-section matches more than one other cross-section in a screen having circular web strings forming the web portion. In contrast, similar parallel plane cross-sections in most commercial screens are effectively the same. That is, any cut made between these two planes will match any other cut. This characteristic extends to cuts in the perpendicular plane as well. Because the present screens may have a circular profile, no more than two cross-sections will match because the length of the cross-section again follows the equation of a circle. Thus, such screens may largely eliminate surfaces that a stream of urine would contact at a roughly 90 degree angle and thereby reduce splash.

In various embodiments, the urinal screen 100 may be molded as a single piece. For example, the urinal screen 100 may be made through injection molding and/or the like. In another embodiment, the urinal screen 100 may be molded from a sheet of polymer material. It should be understood that the urinal screen 100 may be manufactured via a variety of methods known and understood in the art.

The urinal screens disclosed herein may be formed from any suitable materials and combinations of materials known and understood in the art. For example, the urinal screens may be formed of suitable polymer materials. In certain embodiments, the urinal screen 100 is formed from a matrix material impregnated with an air freshening substance selected from an odor-combatting composition, a fragrance, and a combination thereof. Thus, the air freshening substance may have a scent or be unscented. As used herein, the terms "air freshener" and "air freshening" refer to substances that treat air by combatting or neutralizing odor, providing a fragrance, or both.

The matrix material and air freshening substance may be selected from various suitable materials known in the art. For example, the matrix material may be a polymer, such as ethylene-vinyl acetate (EVA). Suitably, EVA has no odor but can be impregnated with a fragrance or odor-combatting composition. Additionally, EVA approaches elastomeric materials in softness and flexibility, yet can be processed like a thermoplastic. In certain embodiments, the EVA polymer of the cartridge body has a number average molecular weight in the range of about 10,000 Daltons to about 100,000 Daltons, or from about 22,000 to about 87,000 Daltons. Other elastomeric or thermoplastic polymers known in the art may also be used in the cartridge body. For example, the polymer of the cartridge body may include ethyl vinyl alcohol, high density polyethylene, low density polyethylene, polystyrene, acrylic polymers, polycarbonates, polyurethanes, nylons, and mixtures and copolymers thereof.

The matrix material may be impregnated with one or more suitable air freshening substances known in the art. For example, suitable air freshening substances may be selected from those compiled by the U.S. Food and Drug Administration in Title 21 of the Code of Federal Regulations, Sections 172.5 10 and 172.5 15. In certain embodiments, the air freshening substance is selected from the group consisting of benzaldehydes, phenols, cinnamic aldehydes and esters, octadienes, dienes, cyclohexadienes, terpenes, and combinations thereof. In some embodiments, the air freshening substance includes triethylene glycol, a bleach, or hydrogen peroxide. Fragrance oils are also suitable for use alone or in combination with other fragrance chemicals. Suitable fragrance oils include, for examples spice oil, flower oil, and fruit oil. Other suitable fragrances include, but are not limited to, benzyl alcohol, ethyl maltol, furaneol, 1-hexanol, cis-3-hexen-1-ol, menthol, benzaldehyde, hexanal, cinnamaldehyde, citral, cis-3-hexenal, furfural, neral, vanillin, ethyl acetate, ethyl butanoate, ethyl decanoate, ethyl hexanoate, ethyl octanoate, hexyl acetate, isoamyl acetate, methyl butanoate, methyl salicylate, pentyl butanoate, pentyl pentanoate, sotolon, strawberry aldehyde, fructone, anethole, anisole, eugenol, dihydrojasmone, 2-acetyl-1-pyrroline, 6-acetyl-2,3,4,5-tetrahydropyridine, gamma-decalactone, gamma-nonalactone, delta-octalactone, jasmine lactone, massoia lactone, camphor, citronellol, linalool, nerol, nerolidol, alpha-terpineol, thujone, and thymol. In certain embodiments, the air freshening substance may include one or more additives, such as hindered amines or antioxidants.

In certain embodiments, the urinal screen contains the air freshening substance in an amount of from about 1 percent by weight to about 75 percent by weight of the impregnated matrix material. In some embodiments, the urinal screen contains the air freshening substance in an amount of from about 10 percent by weight to about 50 percent by weight. In some embodiments, the urinal contains the air freshening substance in an amount of from about 20 percent by weight to about 50 percent by weight. In some embodiments, the urinal screen contains the air freshening substance in an amount of from about 30 percent by weight to about 40 percent by weight. In one embodiment, the urinal screen contains the air freshening substance in an amount of about 25 percent by weight. In one embodiment, the urinal screen contains the air freshening substance in an amount of about 35 percent by weight. The ratio of air freshening substance to matrix material in the urinal screen may be selected to provide the desired release of the air freshening substance.

Example

Urinal screens according to the present disclosure were manufactured and tested for splash reduction performance. In particular, circular rubber urinal screens having web strings with a circular cross-section (e.g., rounded profile) and a diameter of 3.175 mm formed in a mesh pattern to define square open areas between the strings were manufactured. The square open areas of the web portions of these screens were formed with various major dimension side lengths (e.g., 1 mm, 5 mm, 6.5 mm, 10 mm, 20 mm, and 30 mm). Screens with open area side lengths of 5 mm, 6.5 mm, and 10 mm were also manufactured with 2.5 mm posts projecting from the nodal intersections of the web strings. The overall screen diameter of each screen was 165 mm. Splash testing was conducted to measure the percent reduction in splash compared to a control (no screen) over five different target areas for duration of 20 seconds at each target.

Specifically, a dry urinal screen was placed inside the bottom of a urinal per the urinal manufacturer's instructions. A simulated urine stream designed to simulate a male of average height using the urinal was applied to each sample, and the area of the splash travelling outside of a designated urinal containment area was measured using blotter paper. The difference in splash reduction when altering the major dimension between the web strings and/or adding posts to the urinal screens compared to the splash reduction of a urinal without a urinal screen was measured. Percent splash reduction was calculated as ((Control area−Test area)/Control area))×100. Negative values for splash reduction indicate that an increase in splash compared to the control of no screen was observed. The results of the tests are shown in Table 1.

TABLE 1

Urinal Screen Prototype Parameters and Percent Splash Reduction

| Sample | Open Area Major Diameter Spacing (mm) | Percent Splash Reduction (%) |
| --- | --- | --- |
| 1 | 1 | −335.83 |
| 2 | 5 | −583.78 |
| 3 | 10 | −166.05 |
| 4 | 20 | 30.22 |
| 5 | 30 | −157.26 |
| 6 | Control (no Screen) | 0 |
| 7 | 5 (with posts) | 81.00 |
| 8 | 6.5 (with posts) | 91.02 |
| 9 | 10 (with posts) | 82.72 |

Generally, it was surprisingly found that the spacing of the mesh drastically influenced the splash performance of the urinal screen. In particular, it was found that the major dimension of the open area of the mesh web portion can be tailored to provide the desired splash reduction. For example, for the particular web string dimensions and mesh pattern used in the prototypes, 20 mesh spacing (i.e., a major dimension of the open areas of 20 mm) demonstrated a 30 percent splash reduction as compared to the control.

Moreover, it was found that the provision of posts on the urine receiving face of the urinal screen provided further splash reduction over the rounded profile web strings alone. In particular, the inclusion of posts results in a significant improvement in splash reduction versus screens of similar geometries without posts. Specifically, the screen having a mesh spacing of 6.5 mm with posts resulted in a 91.02% reduction, compared to 81.00% reduction by 5 mm spacing with posts and 82.72% reduction by the 10 mm spacing with posts.

Thus, urinal screen that are functional to screen debris and provide drainage while also reducing the splash of urine during use, as compared to commercially available screens and urinals without screens, and optionally with air freshening characteristics, have been developed. Such urinal screens advantageously reduce the splashing of the fluid stream incident thereon by presenting a reduced area of surfaces that are substantially flat to the user's view and/or by providing posts having a size and geometry selected to absorb some of the momentum of a splashed fluid stream and redirect the fluid back toward the urinal floor. Such urinal screens thereby solve the problems of splash common in known urinal screen having flat surfaces and limited or no splash reducing features.

While the disclosure has been described with reference to a number of example embodiments, it will be understood by those skilled in the art that the invention is not limited to such embodiments. Rather, the invention can be modified to incorporate any number of variations, alterations, substitutions, or equivalent arrangements not described herein, but which are commensurate with the spirit and scope of the invention. Additionally, while various example embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A urinal screen, comprising:
   an outer ring;
   a substantially planar web portion bounded by the outer ring and having a first face and an opposed second face, the web portion comprising a plurality of web strings disposed in a mesh pattern, such that a plurality of open areas are defined between the web strings; and
   a plurality of posts projecting from the first face of the web portion, the posts being spaced from one another at a distance greater than a major cross-sectional dimension of the posts, such that surfaces of the web strings extend between the posts,
   wherein surfaces of the web strings extending between the posts and forming the first face of the web portion have a curved surface contour.

2. The urinal screen of claim 1, wherein the open areas of the web portion have a major dimension of from about 1 mm to about 30 mm in plan view.

3. The urinal screen of claim 1, wherein at least a portion of the plurality of posts project from nodes formed by intersections of two of the plurality of web strings.

4. The urinal screen of claim 1, wherein each of the plurality of posts comprises a substantially rounded tip and a body having a substantially rounded surface profile.

5. The urinal screen of claim 4, wherein the surfaces of the web strings and the plurality of posts form a urine receiving face and are configured such that an impinging stream of fluid on the urine receiving face does not contact a flat surface of the web strings or the plurality of posts.

6. The urinal screen of claim 1, wherein each of the plurality of posts has a height of from about 0.5 mm to 1 cm.

7. The urinal screen of claim 1, wherein the plurality of web strings comprise a first set of the web strings that are substantially parallel to one another and a second set of the web strings that are substantially parallel to one another and are substantially perpendicular to the first set of web strings.

8. The urinal screen of claim 7, wherein the open areas are substantially square in plan view.

9. The urinal screen of claim 1, wherein the mesh pattern is a plain weave pattern in which the plurality of web strings appear to be woven over and under each other as warp and weft of a plain weaving.

10. The urinal screen of claim 1, wherein the second face comprises an elevational feature configured to elevate at least a portion of the web portion off of a urinal floor, wherein the elevational feature comprises a plurality of posts or ribs projecting from or integral with the second face of the web portion.

11. The urinal screen of claim 1, wherein the urinal screen comprises ethylene-vinyl acetate impregnated with an air freshening substance for release.

12. A urinal screen, comprising:
    an outer ring having a first side and an opposed second side; and
    a substantially planar web portion bounded by the outer ring and having a first face and an opposed second face, the web portion comprising a plurality of web strings disposed in a mesh pattern, such that a plurality of open areas are defined between the web strings;
    wherein the urinal screen has a urine receiving face and an opposed urinal contacting face, the urine receiving face comprising the first side of the outer ring and the first face of the web portion,
    wherein the open areas of the web portion have a major dimension of from about 1 mm to about 30 mm in plan view,
    wherein the web strings forming the first face of the web portion have a curved surface contour and the first side of the outer ring has a curved surface contour, such that the surfaces of the web strings and the outer ring forming the urine receiving face are not flat in plan view.

13. The urinal screen of claim 12, wherein the open areas of the web portion have a major dimension of from about 5 mm to about 10 mm in plan view.

14. The urinal screen of claim 12, further comprising a plurality of posts projecting from the first face of the web portion, wherein each of the plurality of posts has a height of from about 0.5 mm to 1 cm.

15. The urinal screen of claim 14, wherein at least a portion of the plurality of posts project from nodes formed by intersections of two of the plurality of web strings.

16. The urinal screen of claim 14, wherein each of the plurality of posts comprises a substantially rounded tip and a body having a substantially rounded surface profile.

17. The urinal screen of claim 14, wherein the posts of the plurality of posts are spaced from one another at a distance greater than a major cross-sectional dimension of the posts, such that surfaces of the web strings extending between the posts form the urine receiving face of the urinal screen.

18. The urinal screen of claim 12, wherein the plurality of web strings comprise a first set of the web strings that are substantially parallel to one another and a second set of the web strings that are substantially parallel to one another and are substantially perpendicular to the first set of web strings.

19. The urinal screen of claim 12, wherein the open areas are substantially square in plan view.

20. The urinal screen of claim 12, wherein the mesh pattern is a plain weave pattern in which the plurality of web strings appear to be woven over and under each other as warp and weft of a plain weaving.

21. The urinal screen of claim 12, wherein the second face comprises an elevational feature configured to elevate at least a portion of the web portion off of a urinal floor, wherein the elevational feature comprises a plurality of posts or ribs projecting from or integral with the second face of the web portion.

22. The urinal screen of claim 12, wherein the urinal screen comprises ethylene-vinyl acetate impregnated with an air freshening substance for release.

23. A urinal screen, comprising:
- a substantially planar web portion bounded by an outer ring and having a first face and an opposed second face, the web portion comprising a plurality of web strings having a substantially circular or elliptical cross-section, the web strings being disposed in a mesh pattern, such that a plurality of open areas are defined between the web strings, the open areas having a major dimension of from about 5 mm to about 10 mm; and
- a plurality of posts projecting from nodes formed at intersections of two of the plurality of web strings on the first face of the web portion, wherein the posts are spaced from one another such that exposed surfaces of the web strings extend between the posts,
- wherein the urinal screen has a urine receiving face comprising the plurality of posts and the exposed surfaces of the web strings extending between the posts on the first face, the urine receiving face being configured to receive a downward stream of urine such that the stream does not contact a flat surface of the web strings or posts of the urine receiving face.

24. The urinal screen of claim 23, wherein the posts are spaced from one another at a distance greater than a major cross-sectional dimension of the posts.

* * * * *